United States Patent [19]
Aida et al.

[11] Patent Number: 5,897,495
[45] Date of Patent: Apr. 27, 1999

[54] ULTRASONIC WAVE MEDICAL TREATMENT APPARATUS SUITABLE FOR USE UNDER GUIDANCE OF MAGNETIC RESONANCE IMAGING

[75] Inventors: Satoshi Aida, Tokyo; Mariko Shibata; Katsuhiko Fujimoto, both of Kanagawa-ken; Yoshiharu Ishibashi, Tokyo; Takuji Suzuki; Yasutoshi Ishihara, both of Kanagawa-ken; Kazuya Okamoto, Saitama-ken, all of Japan

[73] Assignee: Kabushiki Kaisha Toshiba, Kawasaki, Japan

[21] Appl. No.: 08/727,036

[22] Filed: Oct. 8, 1996

Related U.S. Application Data

[62] Division of application No. 08/207,670, Mar. 9, 1994, Pat. No. 5,590,653.

[30] Foreign Application Priority Data

Mar. 10, 1993 [JP] Japan .................................... 5-049551

[51] Int. Cl.$^6$ .................................................... A61B 5/055
[52] U.S. Cl. .................................................. 600/411; 601/4
[58] Field of Search .................................. 600/410, 411, 600/439, 459, 407, 472; 324/309, 318; 601/2, 4

[56] References Cited

U.S. PATENT DOCUMENTS

| | | | |
|---|---|---|---|
| 4,526,168 | 7/1985 | Hassler et al. | 128/303 R |
| 4,543,959 | 10/1985 | Sepponen | 128/653.2 |
| 4,620,546 | 11/1986 | Aids et al. | 128/660 |
| 4,960,170 | 10/1990 | Aida et al. | 128/24 |
| 5,033,456 | 7/1991 | Pell et al. | 128/660.03 |
| 5,060,650 | 10/1991 | Wurster et al. | 128/660.3 |
| 5,131,392 | 7/1992 | Jolesz et al. | 600/411 |

(List continued on next page.)

FOREIGN PATENT DOCUMENTS

| | | |
|---|---|---|
| 0 194 897 | 9/1986 | European Pat. Off. . |
| 0 558 029 | 9/1993 | European Pat. Off. . |
| 4-53533 | 2/1992 | Japan . |
| 5-137733 | 6/1993 | Japan . |
| 5-220152 | 8/1993 | Japan . |
| 5-300910 | 11/1993 | Japan . |
| 89/07907 | 9/1989 | WIPO . |
| 90/04360 | 5/1990 | WIPO . |
| 91/11958 | 8/1991 | WIPO . |

OTHER PUBLICATIONS

Hoshi, S. et al., "High Energy Underwater Shock Wave Treatment on Implanted Urinary Bladder Cancer in Rabbits", The Journal of Urology, vol. 146, pp. 439–443 (Aug. 1991).

Jolesz, F. et al., "Laser Surgery Benefits from Guidance by MR", Diagnostic Imaging, pp. 103–108, (Sep. 1990).

Cline, H. et al., "MR–Guided Focused Ultrasound Surgery", Journal of Computer Assisted Tomography, vol. 16, pp. 956–965 (1992).

Primary Examiner—Brian Casler
Attorney, Agent, or Firm—Foley & Lardner

[57] ABSTRACT

An ultrasonic wave medical treatment apparatus capable of preventing the displacement of the focal point of the ultrasonic waves from the treatment target portion within the patient, eliminating a need for re-positioning of the ultrasonic wave applicator with respect to the patient, and taking MR images to be utilized during the treatment at a high resolution. In this apparatus, the ultrasonic wave applicator can be integrally incorporated within a treatment table for carrying the patient into the MRI gantry for taking the MR images. The surface coil for taking the MR images can be provided on a surface film of a water bag in the ultrasonic wave applicator, or on a body cavity probe on which the ultrasonic transducer is also provided. The mixing rate of the coupling fluid can be adjusted, and the impedance matching between the ultrasonic transducer and the driving circuit can be maintained by minimizing the reflected electric power from the ultrasonic transducer.

15 Claims, 18 Drawing Sheets

U.S. PATENT DOCUMENTS

| | | | |
|---|---|---|---|
| 5,146,924 | 9/1992 | Sepponen | 600/411 |
| 5,247,935 | 9/1993 | Cline et al. | 128/653.2 |
| 5,275,165 | 1/1994 | Ettinger et al. | 128/653.2 |
| 5,291,890 | 3/1994 | Cline et al. | 128/653.2 |
| 5,316,000 | 5/1994 | Chapelon et al. | 128/660.3 |
| 5,323,779 | 6/1994 | Hardy et al. | 600/411 |
| 5,368,032 | 11/1994 | Cline et al. | 128/653.2 |
| 5,485,839 | 1/1996 | Aida et al. | 600/411 |

FIG. 11
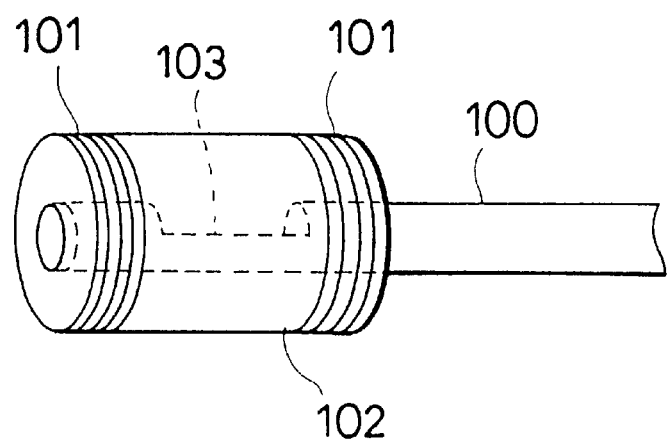
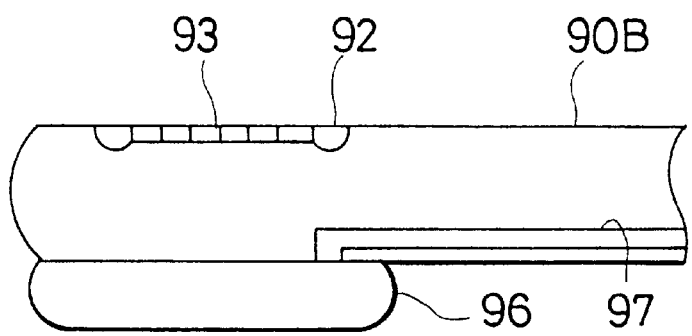
FIG. 12A
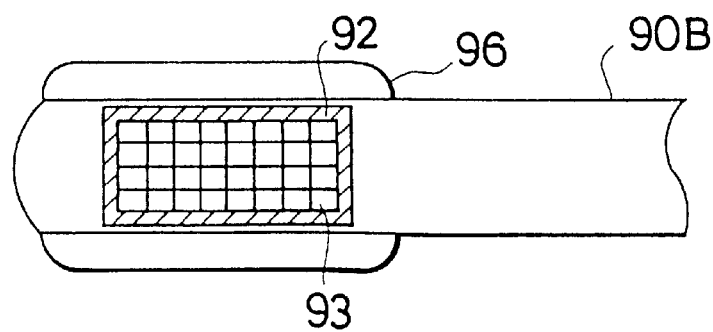
FIG. 12B

FIG. 13A
FIG. 13B
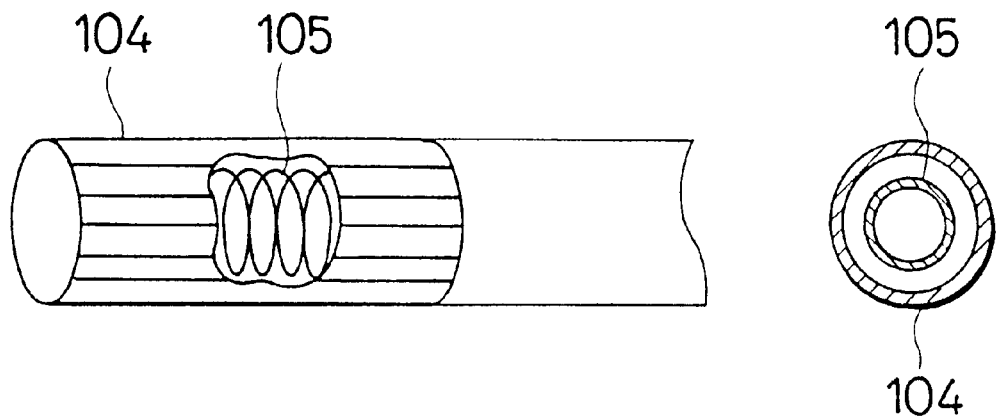
FIG. 14
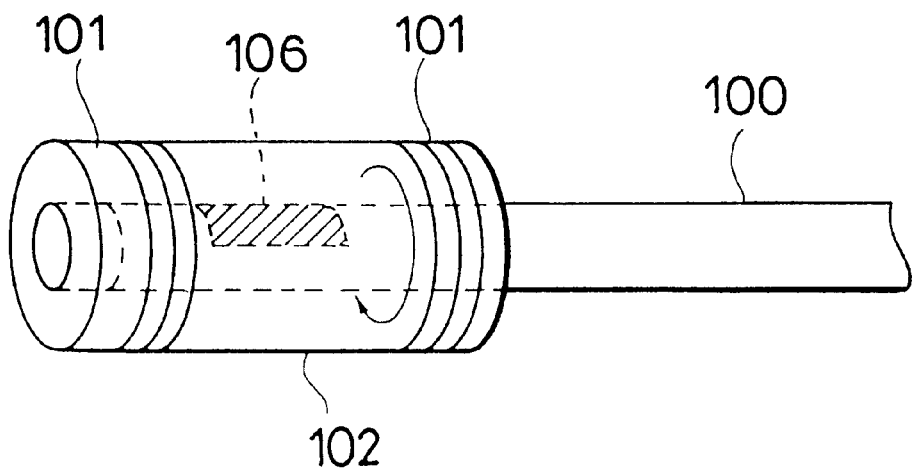

$T_1 = L/C_1$ $T_2 = (L-D)C_1 + D/C_2$

FIG. 21A
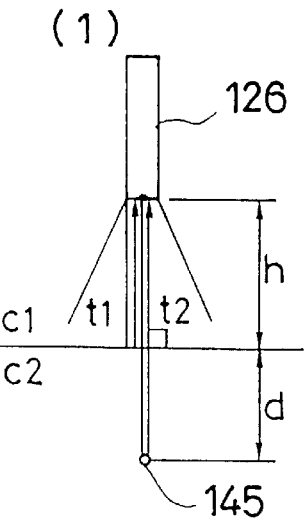
$c_1 = 2h/t_1$
$d = c_2((t_1-t_2)/2)$
FIG. 21B
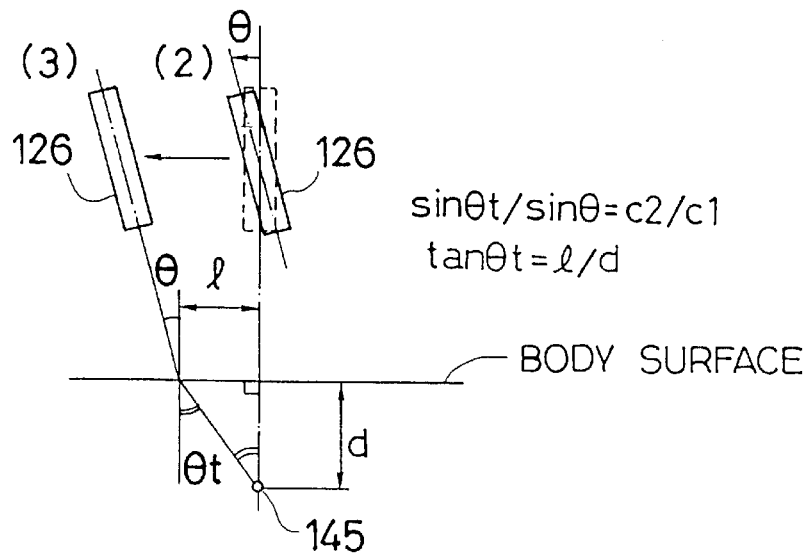
$\sin\theta_t/\sin\theta = c_2/c_1$
$\tan\theta_t = \ell/d$
FIG. 21C  FIG. 21D  FIG. 21E
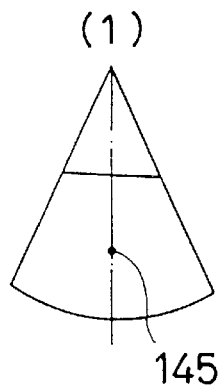   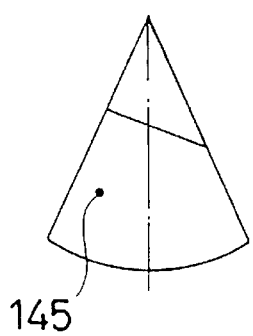   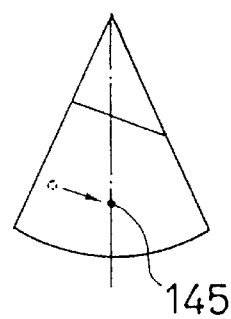

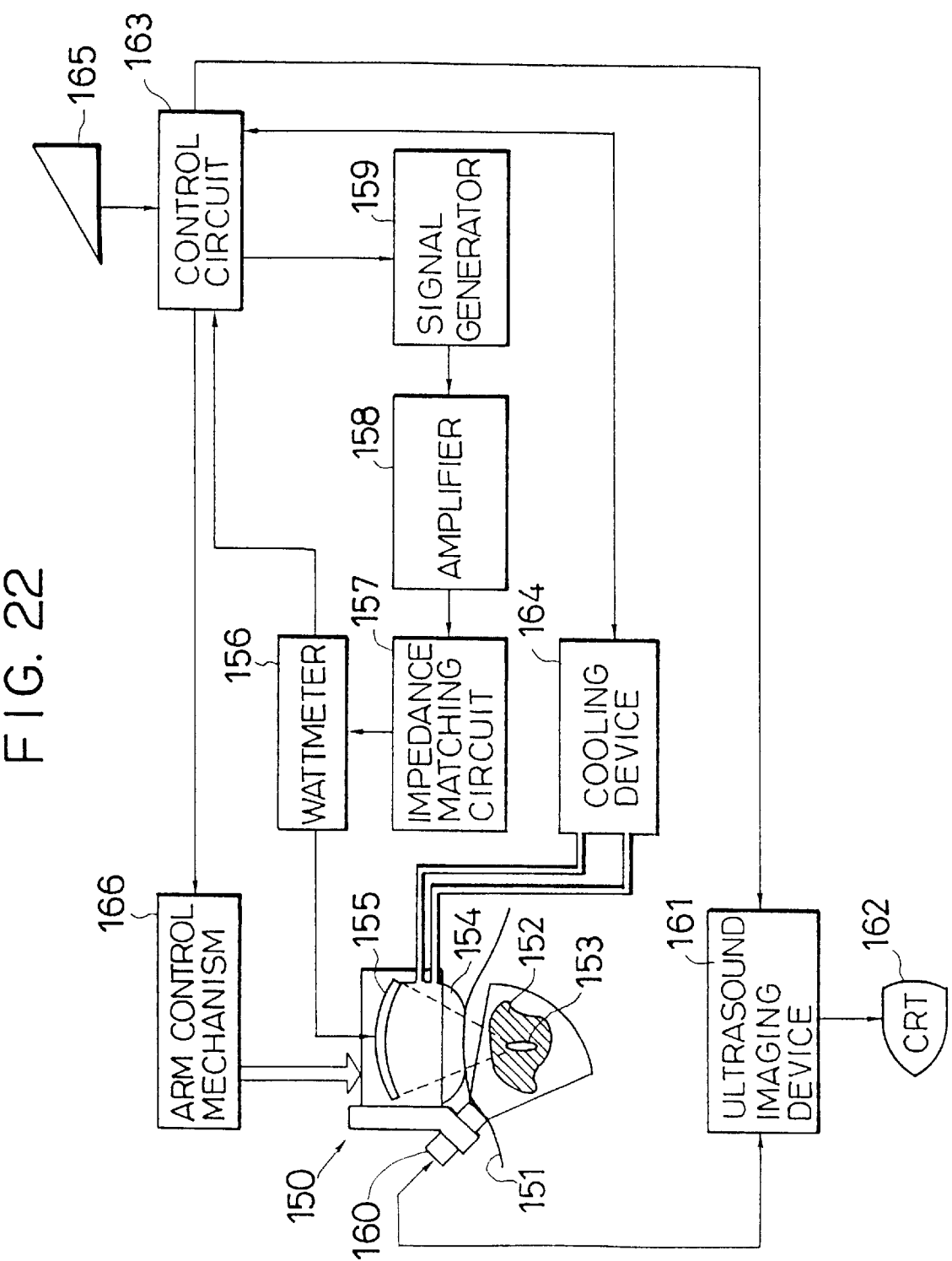

$$L = \sqrt{Z_0 Z_L}/2\pi f$$
$$C = 1/(2\pi f \sqrt{Z_0 Z_L})$$
$$(2\pi f)^2 LC = 1$$

ULTRASONIC WAVE MEDICAL TREATMENT APPARATUS SUITABLE FOR USE UNDER GUIDANCE OF MAGNETIC RESONANCE IMAGING

This application is a division, of application Ser. No. 08/207,670, filed Mar. 9, 1994 now U.S. Pat. No. 5,590,653.

BACKGROUND OF THE INVENTION

1. Field of the Invention

The present invention relates to an ultrasonic wave medical treatment apparatus for treating treatment targets such as tumors, calculi, etc. inside a living body by applying intense ultrasonic waves from an outside of the living body or a body cavity of the living body, under the guidance of the magnetic resonance imaging (MRI).

2. Description of the Background Art

In recent years, for a treatment of the calculosis, much attention has been attracted to a lithotriptor for destroying calculi inside a living body non-invasively by externally applying intense ultrasonic waves focused on the calculi.

Also, for a treatment of the tumors, much attention has been attracted to a hyperthermia for heating the tumor tissues at the temperature over 42.5° C., and a thermal treatment for causing a thermal degeneration by heating at the high temperature over 60° C.

In order to carry out these treatments, there are many propositions for an apparatus for focusing the intense ultrasonic waves generated outside of the living body onto a treatment target portion within the living body, and thermally treating a cancer by the heat generation of the cancer tissue due to the absorption of the ultrasonic energy, such as those disclosed in U.S. Pat. No. 4,620,546, and Japanese Patent Application Laid Open No. 5-137733 (1993). This latter reference proposes a unified configuration of the lithotritor and a thermal treatment apparatus, noting that these tow apparatuses have similar structures.

On the other hand, the researches are also carried out for a treatment method to kill the cancer tissue by the mechanical force of the pulse shaped shock waves having sufficient intensity to destroy the calculi which are irradiated onto the cancer, as disclosed in Hoshi, S. et al.: "High Energy Underwater Shock Wave Treatment on Implanted Urinary Bladder Cancer in Rabbits", Journal of Urology, Vol. 146, pp. 439–443, August, 1991.

Now, in positioning the focus in such a cancer treatment apparatus, the two dimensional ultrasound tomographic images are usually utilized, but this use of the two dimensional tomographic images makes it very difficult to carry out a thorough treatment of the entire tumor as the actual tumor often has a complicated three dimensional shape. For this reason, there has been a proposition to employ the three dimensional ultrasound images instead of the ultrasound tomographic images as disclosed in European Patent No. 0 194 897.

However, in the ultrasound images, the region behind the pneumatic organs such as the bones and the lung becomes invisible, so that the accurate three-dimensional information cannot be obtained even when the three dimensional ultrasound images are utilized.

Furthermore, in the conventional ultrasonic wave medical treatment apparatus, only the relative position of the focal point and the treatment target portion can be ascertained at best, and there has been no means for judging the effect of the treatment, so that the decision for the continuation or termination of the treatment cannot be made until several weeks to several months after the treatment. For these reasons, there has been a proposition for an ultrasonic wave medical treatment apparatus incorporating the MRI or the X-ray CT (computed tomography) as disclosed in Japanese Patent Application Laid Open No. 5-300910 (1993).

In this regard, it is known that the tissue degeneration due to the heat can be confirmed by taking the T2 weighted images using the MRI, as reported in Jolesz, F. A. et al.: "Laser Surgery Benefits from Guidance by MR", Diagnostic Imaging, pp. 103–108, September 1990. Consequently, by observing the difference between the T2 weighted images taken before and after the treatment, it becomes possible to judge the effect of the treatment, so that the treatment can be carried out while checking the untreated portion and the sufficient treatment effect can be secured by a minimum amount of the shock wave irradiation.

It is also possible to set up a treatment plan concerning the scanning method and range for the shock wave focal point, and the intensity, period, and interval for the shock wave irradiation, according to the frozen image obtained by the MRI. Here, however, even when such a treatment plan is prepared, the accurate treatment cannot be expected unless the accurate positioning of the shock wave focal point is guaranteed.

In the conventional ultrasonic wave medical treatment apparatus, it has been necessary to remove the ultrasonic wave applicator from the patient at a time of moving the patient in and out of the MRI gantry, due to the mechanism for moving the ultrasonic wave applicator and the structural properties of the treatment bed and the MRI gantry.

For example, at the beginning of the treatment, after the MR images is taken before the treatment in order to set up the treatment plan, the patient is moved out of the MRI gantry once in order to attach the ultrasonic wave applicator, and then after the positioning of the intense ultrasonic wave focal point with respect to the treatment target portion is made by using the MR images and the ultrasound images, the actual treatment is started. In addition, in a case of carrying out the treatment while judging the treatment effect and checking the untreated portion by the MR images, it is necessary to repeat the operation in which the ultrasonic wave applicator is removed from the patient once and the patient is moved into the MRI gantry in order to take the MR images, and after the treatment effect is judged, the patient is moved out of the MRI gantry again in order to attach the ultrasonic wave applicator, and then after the positioning of the ultrasonic wave focal point is re-established, the treatment is resumed.

In re-establishing the positioning of the ultrasonic wave focal point, even when the relative position of the ultrasonic transducer and the treatment target portion is memorized accurately at a time of the initial positioning, the focal point position can be displaced by a slight movement of the patient. In particular, when it is necessary to repeat the attaching and removing of the ultrasonic wave applicator for a number of times, the probability for the focal point position to be displaced from a desired position becomes large.

Moreover, when the ultrasonic wave applicator is simply pressed against the body surface of the patient, there is a danger for the body surface to move with respect to the ultrasonic wave applicator due to the respiration movement.

Now, there is a recent proposition for mounting the ultrasonic transducer on a catheter, and inserting this catheter into the patient's body under the guidance of the MRI to establish the positioning of the ultrasonic transducer and the treatment target portion, so as to treat the treatment target portion by irradiating intense ultrasonic waves from the ultrasonic transducer mounted on the catheter, as disclosed in Japanese Patent Application Laid Open No. 4-53533 (1993).

In this proposition, when the receiving system of the MRI is for the entire body, the S/N ratio becomes insufficient for the treatment plan set up, the accurate treatment effect judgement, and the real time treatment monitoring, so that it is necessary to use a surface coil to be placed on the body surface in order to obtain the MR images at a sufficiently high S/N ratio. However, because of the presence of the ultrasonic wave applicator on the body surface near the treatment target portion, it is impossible to place this surface coil on the body surface near the treatment target portion during the ultrasonic wave medical treatment. Also, when a surface coil is used for the receiving system of the MRI, the positioning of the receiving system to image the desired treatment target portion at a high S/N ratio becomes difficult as the surface coil has a relatively large sensitivity fluctuation. Moreover, when the ultrasonic transducer is mounted on the catheter and the ultrasonic waves are irradiated from a body cavity, the surface coil cannot be position near the treatment target portion, so that the sufficient MR images of the treatment target portion cannot be obtained.

On the other hand, in the conventional piezoelectric type ultrasonic wave medical treatment apparatus, the focal point is extremely small, so that in the treatment method such as that for causing the thermal degeneration on the tissues by heating the localized region at a high temperature over 80° C. or that for destroying the tissues mechanically by the shock waves, the displacement of the focal point position can lead to the destroying of the normal tissues, unlike the treatment method such as the hyperthermia which carries out the treatment by utilizing the difference in the thermal sensitivity of the tissues. For this reason, it has been necessary to make a highly accurate positioning in the conventional piezoelectric type ultrasonic wave medical treatment apparatus, but there has been a danger that the treatment target portion can be moved due to the respiration or the body movement of the patient, or that the focal point position can be shifted due to the reflection of the ultrasonic waves at the body surface.

In addition, as the focal point is de-focused by the reflection of the ultrasonic waves, there has been a possibility that the temperature at the focal point does not reach to an expected level or that the treatment becomes insufficient as the intensity of the shock waves becomes insufficient. As a consequence, the burden on the patient as well as the physician can be increased by the re-treatment required by the recurrence of the cancer due to the insufficient treatment. Furthermore, there is a danger than the treatment in an accurate range cannot be made as the focal point size becomes larger due to the de-focusing of the focal point.

There is also a need to take an impedance matching between the driving circuit and the ultrasonic transducer in the ultrasonic wave medical treatment apparatus. However, because the piezoelectric element used as the ultrasonic transducer has a high Q at the mechanical resonance point, the impedance matching between the piezoelectric element and the amplifier can be displaced during the treatment due to the change of the characteristic caused by the heat generation of the piezoelectric element, such that there is a danger for failing to obtain the expected acoustic output.

Also, due to the displacement of the impedance matching, the reflected electric power of the ultrasonic transducer can be increased such that there is a possibility for the electro-acoustic conversion efficiency to be deteriorated.

Moreover, in a treatment method in which the malignant tumor tissue located at the focal point is killed by heat, the negative pressure at the focal point becomes large as the focal point input power is large, such that the stable cavitations can be generated and grown as the intense ultrasonic waves are applied continuously, and there is a possibility that the sufficient power cannot reach to the intended focal point due to the scattering of the ultrasonic waves by the cavitations. In addition, there has been a possibility for the appearance of a hot spot at an unexpected location due to the heat generation by the scattered ultrasonic waves.

SUMMARY OF THE INVENTION

It is therefore an object of the present invention to provide an ultrasonic wave medical treatment apparatus capable of preventing the displacement of the focal point of the ultrasonic waves from the treatment target portion within the patient during the treatment.

It is another object of the present invention to provide an ultrasonic wave medical treatment apparatus capable of eliminating a need for re-positioning of the ultrasonic wave applicator with respect to the patient during the treatment.

It is another object of the present invention to provide an ultrasonic wave medical treatment apparatus capable of carrying out the ultrasonic wave medical treatment while taking MR images to be utilized during the treatment at a high resolution.

It is another object of the present invention to provide an ultrasonic wave medical treatment apparatus capable of compensating the deviation of the impedance matching between the ultrasonic transducer and the driving circuit during the treatment.

According to one aspect of the present invention there is provided an ultrasonic wave medical treatment apparatus, comprising: MRI means for taking MR images of a patient in an MRI gantry; and ultrasonic wave treatment means for treating a treatment target portion within the patient by irradiating ultrasonic waves thereon in accordance with the MR images taken by the MRI means, including ultrasonic wave applicator for generating ultrasonic waves focused onto the treatment target portion which is integrally incorporated within a treatment table for carrying the patient into the MRI gantry.

According to another aspect of the present invention there is provided an ultrasonic wave medical treatment apparatus, comprising: MRI means for taking MR images of a patient, including a surface coil for receiving MR signals in taking the MR images; and ultrasonic wave treatment means for treating a treatment target portion within the patient by irradiating ultrasonic waves thereon in accordance with the MR images taken by the MRI means, including ultrasonic wave applicator for generating ultrasonic waves focused onto the treatment target portion having an ultrasonic transducer for generating the ultrasonic waves and a water bag for containing a coupling fluid for leading the ultrasonic waves generated by the ultrasonic transducer to a body surface of the patient by making a contact with the body surface, wherein the surface coil of the MRI means is attached on a surface film of the water bag which makes the contact with the body surface.

According to another aspect of the present invention there is provided an ultrasonic wave medical treatment apparatus, comprising: MRI means for taking MR images of a patient; and ultrasonic wave treatment means for treating a treatment target portion within the patient by irradiating ultrasonic waves thereon in accordance with the MR images taken by the MRI means, including ultrasonic wave applicator for generating ultrasonic waves focused onto the treatment target portion having spike shaped pointers for pointing a focal point of the ultrasonic waves.

According to another aspect of the present invention there is provided an ultrasonic wave medical treatment apparatus, comprising: MRI means for taking MR images of a patient, including a surface coil for receiving MR signals in taking the MR images; and ultrasonic wave treatment means for treating a treatment target portion within the patient by irradiating ultrasonic waves thereon in accordance with the MR images taken by the MRI means, including body cavity probe to be inserted into a body cavity of the patient near the treatment target portion having an ultrasonic transducer for generating ultrasonic waves focused onto the treatment target portion, wherein the surface coil of the MRI means is provided on the body cavity probe.

According to another aspect of the present invention there is provided an ultrasonic wave medical treatment apparatus, comprising: ultrasonic wave applicator for treating a treatment target portion within the patient by irradiating ultrasonic waves focused onto the treatment target portion; and support means for fixedly supporting the ultrasonic wave applicator with respect to the treatment target portion of the patient.

According to another aspect of the present invention there is provided an ultrasonic wave medical treatment apparatus, comprising: ultrasonic wave applicator for treating a treatment target portion within the patient by irradiating ultrasonic waves focused onto the treatment target portion, including an ultrasonic transducer for generating the ultrasonic waves and a water bag for containing a coupling fluid for leading the ultrasonic waves generated by the ultrasonic transducer to a body surface of the patient by making a contact with the body surface; and coupling fluid adjustment means for adjusting a mixing rate of a water and a coupling adjustment agent forming the coupling fluid contained in the water bag according to a temperature of the coupling fluid in the water bag.

According to another aspect of the present invention there is provided an ultrasonic wave medical treatment apparatus, comprising: ultrasonic wave applicator for treating a treatment target portion within the patient by irradiating ultrasonic waves focused onto the treatment target portion, including an ultrasonic transducer for generating the ultrasonic waves; and driving circuit means for driving the ultrasonic transducer to generate the ultrasonic waves; impedance matching circuit means for making an impedance matching between the ultrasonic transducer and the driving circuit means; and control means for controlling one of the driving circuit means and the impedance matching circuit means to make a reflected electric power from the ultrasonic transducer minimum.

According to another aspect of the present invention there is provided an ultrasonic wave medical treatment apparatus, comprising: ultrasonic wave applicator for treating a treatment target portion within the patient by irradiating ultrasonic waves focused onto the treatment target portion, including an ultrasonic transducer for generating the ultrasonic waves; and driving circuit means for driving the ultrasonic transducer to generate the ultrasonic waves; and control means for changing a driving frequency of the driving circuit means while the ultrasonic wave applicator irradiates the ultrasonic waves onto the treatment target portion.

Other features and advantages of the present invention will become apparent from the following description taken in conjunction with the accompanying drawings.

BRIEF DESCRIPTION OF THE DRAWINGS

FIG. 11 is a perspective view of another modified configuration for the body cavity probe in the third embodiment of the present invention.

FIGS. 12A and 12B are cross sectional and plan views, respectively, of another modified configuration for the body cavity probe in the third embodiment of the present invention.

FIGS. 13A–13B are perspective views of another modified configuration for the body cavity probe in the third embodiment of the present invention.

FIG. 14 is a perspective view of another modified configuration for the body cavity probe in the third embodiment of the present invention.

FIGS. 21A, 21B, 21C, 21D, and 21E are illustrations showing another scheme for measuring sonic speeds in the apparatus of FIG. 19.

FIG. 22 is a partially cross sectional block diagram of a fifth embodiment of an ultrasonic wave medical treatment apparatus according to the present invention.

DETAILED DESCRIPTION OF THE PREFERRED EMBODIMENTS

Figure 1:
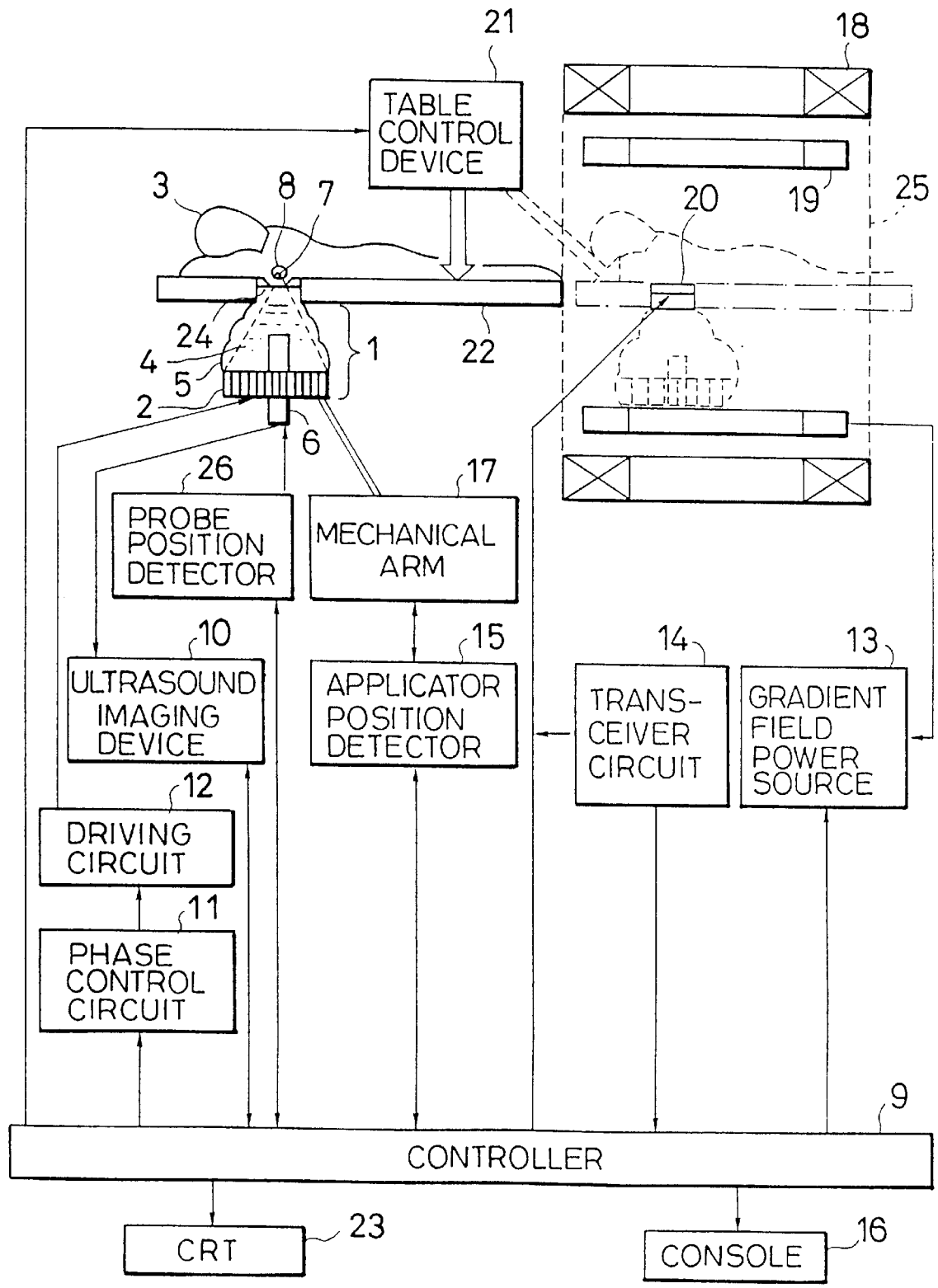
FIG. 1 is a block diagram of of the first embodiment of an ultrasonic wave medical treatment apparatus according to the present invention.

Referring now to FIG. 1, the first embodiment of the ultrasonic wave medical treatment apparatus according to the present invention will be described in detail. This first embodiment concerns with an overall configuration of the apparatus which is suitable for use in conjunction with the MRI.

Figure 2:
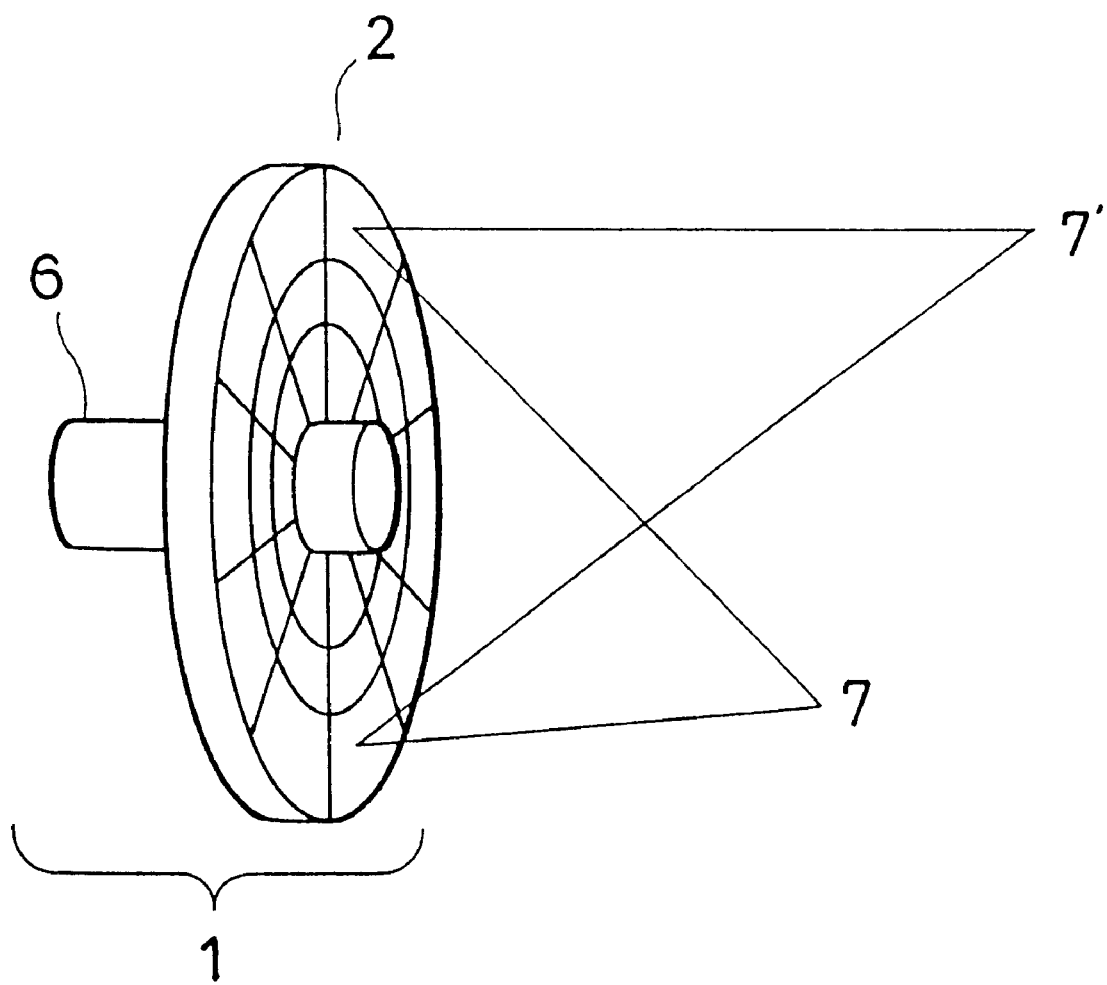
FIG. 2 is a perspective view of a phased array type ultrasonic transducer used in the apparatus of FIG. 1.

In this ultrasonic wave medical treatment apparatus of FIG. 1, an ultrasonic wave applicator 1 is integrally incorporated by being fixedly attached below a treatment hole 24 formed on the treatment table 22, with its orientation made to be finely adjustable by a mechanical arm 17. This ultrasonic wave applicator 1 comprises an ultrasonic transducer 2 for generating intense ultrasonic waves for treatment, a water bag 5 containing a coupling fluid 4 for leading the intense ultrasonic waves to the patient 3 through the treatment hole 24, and an ultrasonic probe 6 for ultrasound imaging provided at a center of the ultrasonic transducer 2, where the ultrasonic transducer 2 has a detailed configuration as shown in FIG. 2 in which a planar disk shaped ultrasonic transducer 2 is divided into a number of channels in radial and circumferential directions while the ultrasonic probe 6 is made to be movable forward and backward as well as rotatable.

Figure 3:
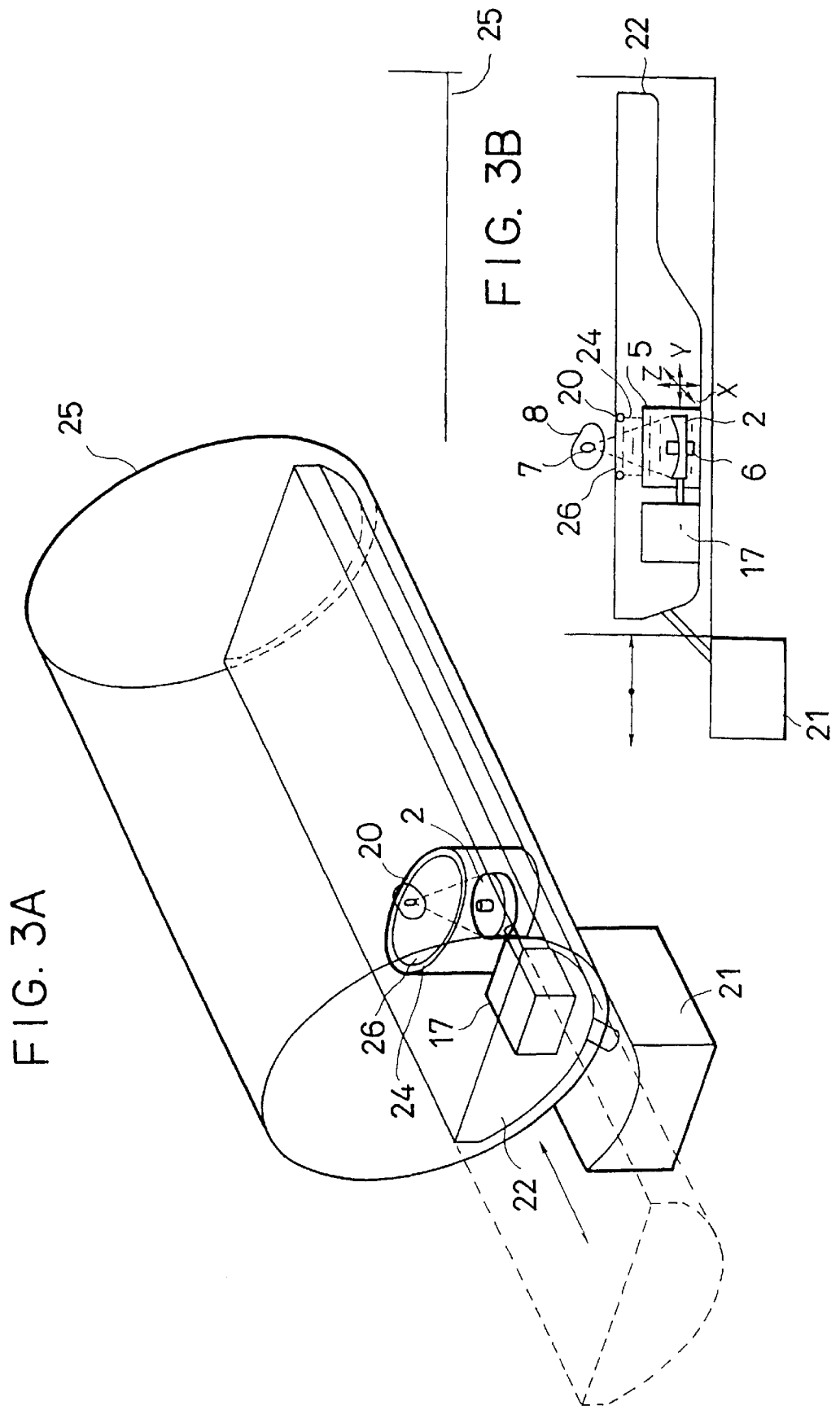
FIGS. 3A and 3B are perspective and side views, respectively, of a treatment table incorporating the ultrasonic wave applicator in the apparatus of FIG. 1.

In this first embodiment, this ultrasonic wave applicator 1 and the mechanical arm 17 are integrally incorporated within the treatment bed 22 as shown in FIGS. 3A and 3B such that the ultrasonic wave applicator 1 moves along with the treatment bed 22 when the treatment bed 22 is controlled to carry the patient 3 in and out of an MRI gantry 25. Here, an upper opening of the treatment hole 24 is covered by a film 26, and in addition, an RF coil 20 for transmitting RF pulses and receiving MR signals in the MRI is provided at a circumference of the treatment hole 24 in advance.

In short, in the treatment, the patient 3 is placed on the treatment table 22 such that the tumor 8 to be treated is located above the treatment hole 24, and the focal point 7 of the intense ultrasonic waves from the ultrasonic transducer 2 is adjusted to be focused onto the tumor 8. Then, the ultrasonic transducer 2 is driven by a driving circuit 12 to actually irradiate the intense ultrasonic waves onto the tumor 8 so as to treat the tumor 8 by maintaining the treatment target portion at a high temperature.

In this first embodiment, the ultrasonic transducer 2 is made to be a phased array type in which the focal point position, the acoustic field, and the heating region can be controlled without moving the ultrasonic wave applicator 1 itself, by controlling the driving timings of the driving circuit 12 by a phase control circuit 11. The driving circuit 12 is divided into a number of channels in correspondence to divided channels of the ultrasonic transducer 2, and each channel is driven by an independent timing signal obtained by appropriately delaying the control signal from a controller 9 at the phase control circuit 11. In this manner, the focal point of the intense ultrasonic waves can be positioned at any desired three dimensional position such as 7 and 7' shown in FIG. 2. The detail concerning the shifting of the focal point position by the delayed timing control is disclosed in U.S. Pat. No. 4,526,168.

Also, the size of the treatment hole 24 can be changed by changing the treatment table 22 according to the size and the shape of the treatment target portion.

Now, after the patient 3 is placed on the treatment table 22 with the treatment target portion located above the treatment hole 24, the position of the tumor 8 is checked by the ultrasound images taken by the ultrasonic probe 6 attached to the ultrasonic wave applicator 1, and an ultrasonic imaging device 10 supplies the data on the relative position of the tumor 8 and the ultrasonic probe 6 at that point to the controller 9. Also, the relative position of the ultrasonic probe 6 and the ultrasonic transducer 2 at that time is determined by a probe position detector 26 and supplied to the controller 9, while the positions of the ultrasonic transducer 2 and the ultrasonic wave applicator 1 with respect to the treatment table 22 at that time is determined by an applicator position detector 15 connected with the mechanical arm 17 and supplied to the controller 9. The controller 9 calculates the relative position of the tumor 8 and the ultrasonic transducer 2 from these position data, and determines and memorizes the focal point position set by the phased array.

This focal point position set by the phased array is supplied from the controller 9 to the ultrasound imaging device 10, such that the ultrasound imaging device 10 can display the state of the tumor 8 at the treatment target portion and the position of the focal point 7 in real time even during the treatment.

Next, the patient 3 is carried into the MRI gantry 25 in which a static field coil 18 and gradient field coils 19 for the MRI are provided, by moving the treatment table 22 by a table control device 21 under the control by the controller 9. At this point, there is no need to remove the ultrasonic wave applicator 1 from the patient 3 as it moves along with the treatment table 22 in a state of being fixedly attached below the treatment hole 24, and consequently there is no need to adjust the positioning of the ultrasonic wave applicator 1 every time the treatment table 22 is moved in and out of the MRI gantry 25.

Here, in order to prevent the disturbance of the magnetic fields used in the MRI due to the ultrasonic wave applicator 1 and the treatment table 22, there is a need to form the ultrasonic wave applicator 1 and the treatment table 22 by non-magnetic materials as much as possible. For example, the treatment table 22 can be made of wood or reinforced plastic, while the ultrasonic wave applicator 1 and the mechanical arm 17 can be made of materials such as reinforced plastic and the austenitic cast iron which has nearly the same mechanical property as the usual cast iron while being non-magnetic, except for wirings connecting the ultrasonic transducer 2 and the driving circuit 12 which must be electrically conductive. It is also possible to make the mechanical arm 17 to be a hydraulic type rather than an electrical type using an electric motor, to further reduce the amount of magnetic material.

When the patient 3 is moved into the MRI gantry 25, the controller 9 activates the gradient field power source 13 for driving the gradient field coils 19 and the transceiver circuit 14 for driving the RF coil 20 according to the pulse sequence specified from a console 16 such as that of the T2 weighted imaging, so as to obtain and store the three dimensional MR images of the patient 3 in a memory.

At this point, it is possible to set up the treatment plan according to the obtained MR images. To this end, the manner of displaying the MR images on a CRT 23, the combined use of the ultrasound images, and a method of setting up the treatment plan are described in detail in Japanese Patent Application Laid Open No. 5-300910 (1993).

When the MR images are obtained, while the patient 3 is still in the MRI gantry 25, the coincidence of the position of the focal point 7 memorized in the controller 9 and the position of the tumor 8 is checked, and the treatment is started as the controller 9 commands the start of the ultrasonic wave irradiation to the driving circuit 12. In this case, there is no need to move the patient 3 out of the MRI gantry for the purpose of carrying out the treatment, so that the time lag between the treatment and the MR image taking can be reduced and the chance for the patient 3 to move during this time lag period can also be reduced.

At a middle or an end of the original treatment plan, the irradiation of the ultrasonic waves is stopped to observe the progress state of the treatment by the procedure similar to that described above. In this case, the MR images in a vicinity of the tumor 8 are taken to examine the change in the living body. During this observation, the ultrasonic wave applicator 1 remains to be attached on the patient 3. Here, by subtracting the T2 weighted MR image taken before the treatment and stored in the memory from the T2 weighted MR image taken after the treatment, the thermally degenerated region can be confirmed very clearly, such that it becomes possible to judge whether the sufficient treatment has been done or more treatment is necessary. This procedure for making the observation may be incorporated into the treatment plan in advance, such that the MR imaging is carried out at predetermined intervals automatically.

When the completion of the sufficient treatment is confirmed by this observation using the MR images, the operator finishes the treatment operation, and the controller 9 can call up the history of the treatment condition from the memory and display it as a treatment record on the CRT 23.

It is to be noted that instead of the RF coil 20 provided on the treatment hole 24, a body cavity probe may be used for the MRI if desired. Moreover, instead of the phased array type ultrasonic transducer, the annular array type or any other suitable type of the ultrasonic transducer may be used if desired. Furthermore, instead of the MRI, the X-ray CT may be used if desired.

As described, according to this first embodiment, it becomes possible to fix the relative position of the ultrasonic wave applicator and the treatment target portion throughout the treatment, so that the danger for the erroneous irradiation of the intense ultrasonic waves or the unexpected oversight due to the displacement of the focal point from the intended treatment target portion can be reduced. Moreover, the re-positioning after each treatment and treatment effect observation can be avoided, so that the entire treatment period can be shortened considerably.

Figure 4:
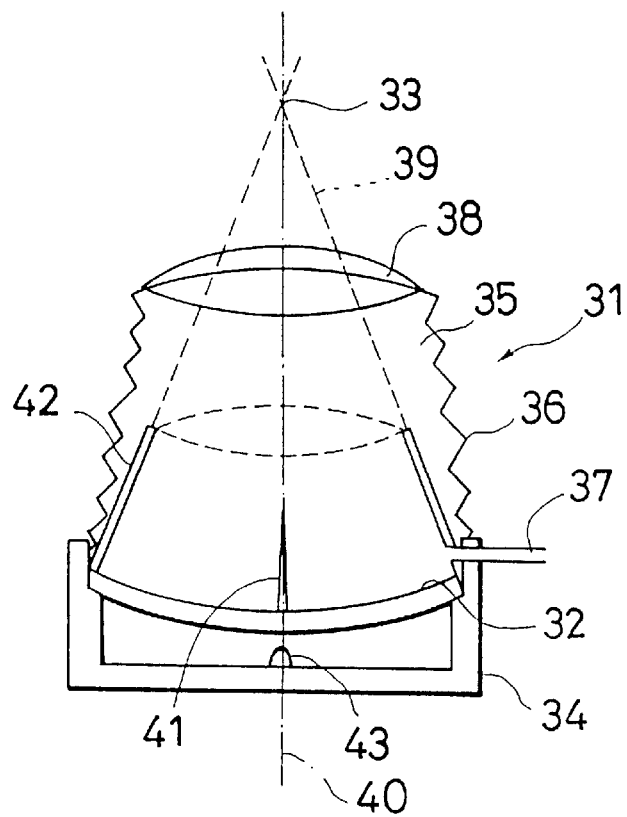
FIG. 4 is a cross sectional view of an ultrasonic wave applicator in the second embodiment of the present invention.

Referring now to FIG. 4, the second embodiment of the ultrasonic wave medical treatment apparatus according to the present invention will be described in detail. This second embodiment concerns with the configuration of the ultrasonic wave applicator that can be used in the ultrasonic wave medical treatment apparatus suitable for use in conjunction with the MRI. Consequently, the ultrasonic wave applicator of this second embodiment described below can be used in the overall configuration similar to that of FIG. 1 instead of the ultrasonic wave applicator 1 of the first embodiment described above.

In this second embodiment, an ultrasonic wave applicator 31 is formed to have a configuration as shown in FIG. 4, which comprises an ultrasonic transducer 32 having a concave surface for generating intense ultrasonic waves for treatment, a housing 34 made of resin for supporting the ultrasonic transducer 32, a water bag 36 containing a coupling fluid 35 for leading the intense ultrasonic waves to the patient, a water pipe 37 provided on the housing 34 for supplying and withdrawing the coupling fluid 35 to and from the water bag 36, and a surface coil 38 for the MRI attached on a surface film of the water bag 36 on an upper side which makes contact with the body surface of the patient.

Here, the ultrasonic transducer 32 has the concave surface such that the generated ultrasonic waves will be propagated within a conical passing route 39 indicated by a dashed line and focused on a focal point 33 located at a center of a curvature of the concave surface. The surface coil 38 is provided on the upper side of the surface film of the water bag 36 such that the passing route 39 of the ultrasonic waves is contained within its opening. This surface coil 38 can be attached on either an inner side or an outer side of the surface film forming the water bag 36.

Thus, when this ultrasonic wave applicator 31 is attached to the patient with the upper side of the surface film of the water bag 36 making a contact with the body surface through ultrasonic jelly, the surface coil 38 can be brought into a tight contact with the body surface as the surface film of the water bag 36 is deformed along the shape of the body surface.

Figure 5:
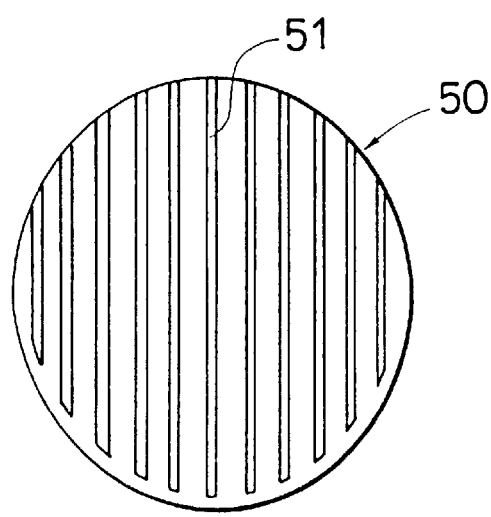
FIG. 5 is a plan view of an electrode to be used for the ultrasonic transducer in the ultrasonic wave applicator of FIG. 4.

Now, in general, the ultrasonic transducer 32 is made of a piezoelectric ceramic which is non-magnetic and non-conductive, but on front and back sides of this ultrasonic transducer 32, electrodes for applying driving voltages to the ultrasonic transducer 32 are provided. Consequently, when the radio frequency magnetic field for the MRI is applied on the ultrasonic wave applicator 31, the eddy currents can be induced on these electrodes, and these eddy currents in turn can disturb the magnetic fields for the MRI to cause the degradation of the image quality in the obtained MR images. In order to avoid this adverse effect of the eddy currents, each electrode 50 attached to the ultrasonic transducer 32 of this second embodiment has a number of slits 52 formed thereon as shown in FIG. 5, so as to reduce the electrical conductivity of the electrode 50 with respect to the eddy currents.

In addition, as shown in FIG. 4, the ultrasonic wave applicator 31 of this second embodiment is further equipped with a needle or rod like spike shaped pointer 41 located along a central axis 40 joining the focal point 33 and a center of the concave surface of the ultrasonic transducer 32, and a plurality of needle or rod like spike shaped pointers 42 located along the circumference of the concave surface of the ultrasonic transducer 32 and pointing along the conical passing route 39 of the generated ultrasonic waves for the purpose of indicating the focal point 33. These pointers 41 and 42 are made of material such as rubber which can be imaged by the MRI but which are flexible enough not to hurt the patient's body even when they touch the body surface of the patient. Furthermore, there is also provided a protrusion 43 on the housing 34 at a position of the central axis 40 as shown in FIG. 4.

Figure 6:
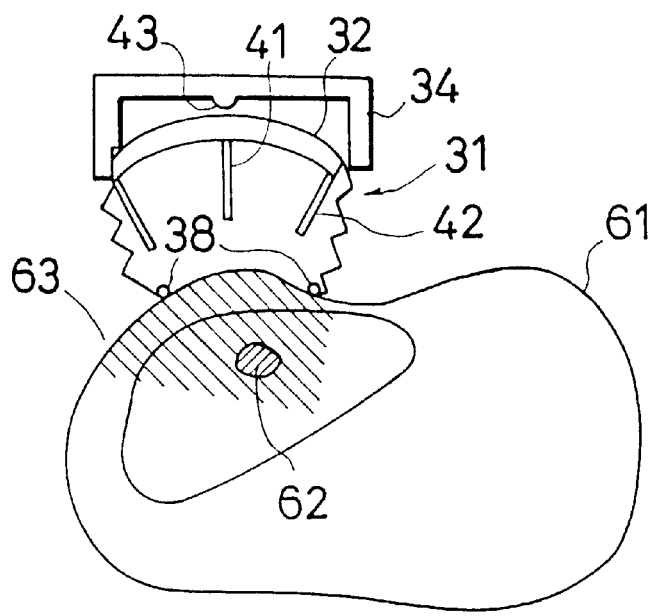
FIG. 6 is an illustration of an MR tomographic image taken while using the the ultrasonic wave applicator of FIG. 4.

When the MR tomographic image is taken in a state in which this ultrasonic wave applicator 31 is attached on the body surface of the patient, the obtained MR tomographic image appears as shown in FIG. 6. In this case, the tomographic image of the whole body of the patient 61 as well as the high resolution image in a vicinity of the treatment target portion are taken together by using the surface coil 38 provided on the ultrasonic wave applicator 31 in conjunction with a whole body coil not shown in the figure. As a result, the tumor 62 which is the treatment target portion appears within the high resolution image region 63 taken by the surface coil 38, while the tomographic image of the patient 61 and the ultrasonic wave applicator 31 also appear in the MR tomographic image taken by the whole body coil.

By observing this MR tomographic image, it is possible to recognize that the tomographic plane of this MR tomographic image contains the central axis 40 of the ultrasonic waves when the pointer 41 and the protrusion 43 are visible on the MR tomographic image, and the focal point 33 of the ultrasonic waves can be determined as an intersection of two lines extended from the pointers 42 on sides of the ultrasonic transducer 32.

In a case the tumor 62 is appearing clearly, but the pointer 41 and the protrusion 43 are not, it is either that the central axis 40 of the ultrasonic waves is on the tumor 62 but angled with respect to the tomographic plane, or that the central axis of the ultrasonic waves is off the tumor 62. Consequently, the operator aligns the tomographic plane of the MRI with the central axis 40 of the ultrasonic waves, and detects the deviation of the tumor 62 in a direction perpendicular to the tomographic plane, and compensate the detected deviation by adjusting the positioning of the ultrasonic wave applicator 31. In this manner, without mechanically measuring the absolute position of the ultrasonic wave applicator 31 in the spatial coordinate of the MRI, the positioning of the ultrasonic wave applicator 31 can be achieved by utilizing the visual inspection of the operator.

Figure 7:
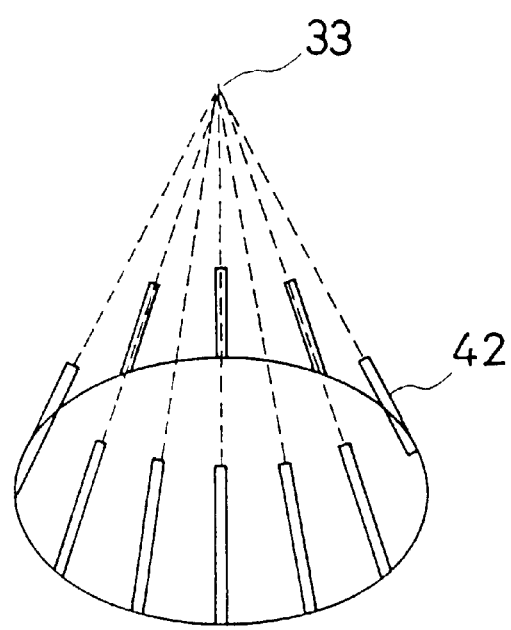
FIG. 7 is an alternative configuration of spike shaped pointers that can be used in the ultrasonic wave applicator of FIG. 4.

It is to be noted that instead of providing the pointers 41 and 42 as described above, only a number of pointers 42 along the circumference of the ultrasonic transducer 32 can be provided in a form shown in FIG. 7 to indicate the position of the focal point 33.

Figure 8A:
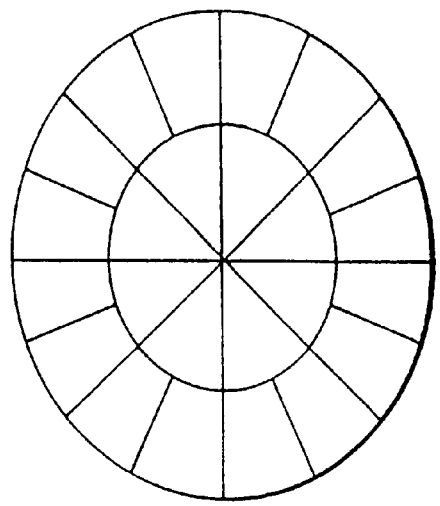
FIG. 8A is a plan view of a phased array type ultrasonic transducer that can be used in the ultrasonic wave applicator of FIG. 4.
Figure 8B:
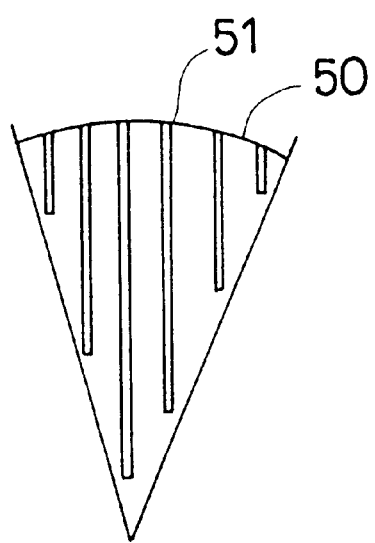
FIG. 8B is a plan view of an electrode to be used for the ultrasonic transducer of FIG. 8A.

Also, instead of the concave shaped single plate ultrasonic transducer 32, a phased array type ultrasonic transducer formed by a plurality of transducer elements as shown in FIG, 8A may be used. In such a case, the slits 51 can be formed on each electrode 50 corresponding to each transducer element as shown in FIG. 8B for example. Also, in a case of the phased array type ultrasonic transducer, the focal point position can be changed electrically, but even in this case, the pointers 41 and 42 of this second embodiment can be utilized advantageously as an indication of a reference point for the focal point.

As described, according to this second embodiment, it becomes possible to obtain the MR images at a high resolution while keeping the ultrasonic wave applicator to be attached on the patient, without affecting the coupling between the patient and the ultrasonic wave applicator, so that the MR images can be obtained even during the treatment.

Figure 9:
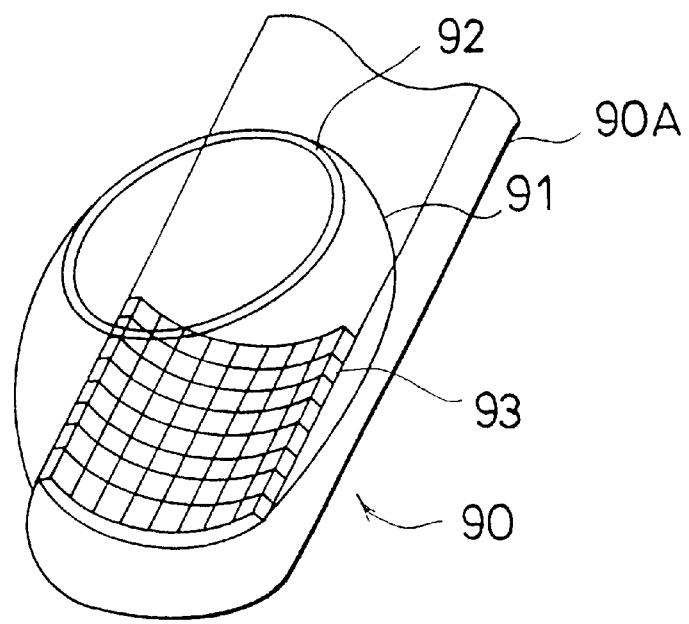
FIG. 9 is a perspective view of a body cavity probe in the third embodiment of the present invention.

Referring now to FIG. 9, the third embodiment of the ultrasonic wave medical treatment apparatus according to the present invention will be described in detail. This third embodiment concerns with the configuration of the ultrasonic wave applicator in a form of a body cavity probe that can be used in the ultrasonic wave medical treatment apparatus suitable for use in conjunction with the MRI. Consequently, the body cavity probe of this third embodiment described below can be used in the overall configuration similar to that of FIG. 1 instead of the ultrasonic wave applicator 1 of the first embodiment described above.

In this third embodiment, a body cavity probe 90 is formed to have a configuration as shown in FIG. 9, which comprises a balloon 91 located at an end of a probe body 90A which is to be expanded by a water supplied from an external water circuit (not shown), a surface coil 92 attached on an upper surface of the balloon 91 which functions as a receiver coil for the MRI, and an ultrasonic transducer 93 located at the end of the probe body 90A below the balloon 91 which is formed by a number of piezoelectric elements to be phase controlled independently from each other. Thus, the ultrasonic transducer 93 of this third embodiment can shift the position of the focal point of the generated ultrasonic waves by appropriately controlling the phases of the piezoelectric elements Just as in the phased array type ultrasonic transducer of the first embodiment described above.

With this configuration of FIG. 9, it is always possible to substantially overlap an imaging region in which the MR images can be taken at a high S/N ratio by the surface coil 92 with an irradiation region in which the focal point of the ultrasonic waves can be shifted by the ultrasonic transducer 93.

At a time of treatment, the position of the treatment target portion is determined first by obtaining the MR image by using a usual external receiver coil (not shown) rather than this body cavity probe 90. Then, this body cavity probe 90 is inserted into a body cavity of the patient to a position from which the treatment target portion can be treated effectively. After the body cavity probe 90 is positioned appropriately within the body cavity, the water is supplied into the balloon 91 to expand it such that the body cavity probe 90 can be fixed at that position as the expanded balloon 91 is pressed against the inner wall of the body cavity. Then, the MR signals generated in response to the application of the RF pulses are received by the surface coil 92, to obtain the MR image of the treatment target portion at a high S/N ratio. Then, according to the obtained MR image, the ultrasonic waves focused onto the treatment target portion are irradiated from the ultrasonic transducer 93 to carry out the treatment. After the treatment, the MR image is obtained again in the similar manner in order to check the treatment effect.

Here, it is to be noted that the initial determination of the treatment target portion may be achieved by monitoring a rough position of the body cavity probe 90 within the body cavity in real time by means of an ultrasound imaging device, or by monitoring the interior of the body cavity in real time by means of an optical fiber used endoscopically, instead of using the MRI as described above. The subsequent positioning of the body cavity probe 90 may also be achieved in these manners.

It is also possible to utilize the surface coil 91 as a transmitter coil for transmitting radio frequency pulses to the treatment target portion such that the thermal treatment can be applied to the treatment target portion by the heat induced by the radio frequency pulses.

It is also possible to utilize the ultrasonic transducer 93 for the purpose of the ultrasound imaging device for monitoring the treatment target portion.

Figure 10:
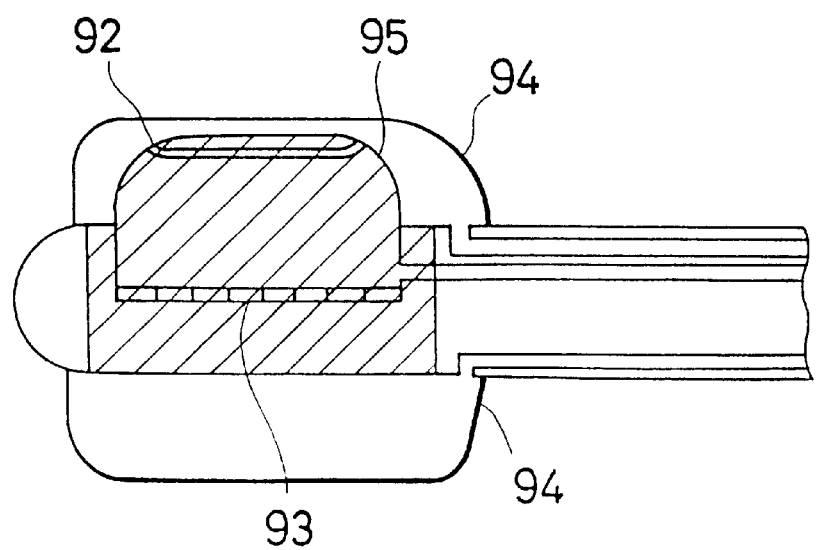
FIG. 10 is a cross sectional view of one modified configuration for the body cavity probe in the third embodiment of the present invention.

In this configuration of FIG. 9, once the balloon 91 is expanded, the positions and the orientation of the body cavity probe 90 is going to be fixed. However, this configuration of FIG. 9 may be modified as shown in FIG. 10 in which the balloon 91 is replaced by double balloons 94 and 95, of which the outer balloon 94 is expanded similarly to the balloon 91, while the inner balloon 95 is formed such that the shaded region having the surface coil 92 and the ultrasonic transducer 93 provided thereon can be freely rotatable, so that the orientation of the surface coil 92 and the ultrasonic transducer 93 can be changed by rotating this rotatable portion of the inner balloon 95 even after the position of the body cavity probe as a whole is fixed by the expanded outer balloon 94.

It is also possible to make this outer balloon 94 to be substantially larger in the axial direction of the probe body 90A such that the inner balloon 95 can be moved in the axial direction as well. In this manner, the positioning with respect to the treatment target portion can be carried out after the body cavity probe 90 is inserted into the body cavity, without determining the treatment target portion in advance by using the MRI.

It such a case, even when the ultrasonic transducer 93 is capable of shifting the focal point position in a depth direction alone, the focal point position of the ultrasonic waves can be shifted three dimensionally by incorporating the rotational and translational movements of the ultrasonic transducer.

Alternatively, the configuration of FIG. 9 may be modified as shown in FIG. 11 in which coils 101 capable of generating a uniform magnetic field in the circumferential direction are provided around a cylindrical balloon 102, while an ultrasonic transducer 103 is provided on a probe body 100 which is both rotatable in the circumferential direction and movable in the axial direction and located within the balloon 102, such that the MR image can be obtained uniformly along the circumferential direction, and the positioning of the body cavity probe can be achieved by fixing the balloon 102 while rotating and moving the probe body 100. In FIG. 11, the coils 101 are made to be solenoid coils wound in opposite directions which are attached at opposite ends of the balloon 102, such that the MR images at a high S/N ratio can be obtained at a region between these two coils 101.

It is to be noted that the water to be supplied into the balloon of the body cavity probe according to this third embodiment should preferably be the ion exchanged water or the pure water rather than the tap water.

It is also possible to replace the water by the other material which can take the acoustic impedance matching. Namely, when the MR image is taken while the balloon of the body cavity probe is filled with the water, a region in the MR image at which the water is present appears brighter than the other regions, and the sensitivity of the other regions which may contain the treatment target portion can be deteriorated. This phenomenon can be suppressed either by detecting the position of the balloon in advance and suppressing the signal originating from the balloon region by appropriate data processing, or by supplying the fat into the balloon instead of the water and suppressing the signal originating from the fat by appropriate data processing which is well known in the MRI. It is equally possible to use the fluid material other than the fat which has the MR frequency distinctly different from that of the living body due to the chemical shift and the acoustic impedance not largely different from that of the living body, and suppressing the signal originating from this fluid material by appropriate data processing.

It is also possible to modify the configuration of FIG. 9 as shown in FIGS. 12A and 12B in which the surface coil 92 and the ultrasonic transducer 93 are provided on the upper side of the probe body 90B such that the surface coil 92 encloses the ultrasonic transducer 93, and a balloon 96 is provided on the lower side of the probe body 90B and filled with an externally supplied air through a pipe 97 formed within the probe body 90B, such that the surface coil 92 and the ultrasonic transducer 93 are pressed against the inner wall of the body cavity directly as the balloon 96 is expanded by the air at the opposite side. In this case, the material to be poured into the balloon 96 is not necessarily limited to the air, and can be anything that can expand the balloon 96.

It is also possible to adapt the body cavity probe of this third embodiment to a catheter for thrombolysis such as that disclosed in Japanese Patent Application Laid Open No. 5-220152 (1993). This catheter for thrombolysis is a device used for injecting the thrombolytic agent in a vicinity of the treatment target portion within the blood vessel and then irradiating the ultrasonic waves onto the treatment target portion so as to improve the treatment effect, although the injection of the thrombolytic agent is not absolutely necessary in every case.

More specifically, the body cavity probe can be formed as shown in FIGS. 13A–B, which has coaxially arranged ultrasonic transducer 104 on an outer side and solenoid coil 105 on an inner side, where the ultrasonic transducer 104 is formed by a number of rectangular piezoelectric elements attached around an outer circumference of the body cavity probe to surround the solenoid coil 105. This body cavity probe of FIGS. 13A–B is to be attached at a tip end of the catheter, such that the MRI images at a high S/N ratio can be obtained uniformly along the circumferential direction to monitor the interior of the blood vessel into which the catheter is inserted for the purpose of observing the treatment effect, while injecting the thrombolytic agent from the catheter and irradiating the ultrasonic waves from the ultrasonic transducer 104.

It is also possible to replace the ultrasonic transducer in the body cavity probe of this third embodiment by the other treatment device such as a laser emitter. For example, the configuration of FIG. 11 can be modified as shown in FIG. 14 in which the ultrasonic transducer 103 is replaced by a laser emitter 106, such that the laser beam can be irradiated onto the treatment target portion around the body cavity by rotating the probe body 100 so as to carry out the thermal or opto-chemical treatment. In this configuration of FIG. 14, in a case of carrying out the thermal treatment, there is a danger for damaging the normal tissues in a vicinity of the body cavity as well, so that water filling inside the balloon 102 should be circulated by an external water circuit for the purpose of cooling.

Here, the opto-chemical treatment is that in which the agent having a tumor selectivity which can reveal the anti-tumor effect upon the irradiation by the laser beam is injected, and then the laser beam is irradiated thereon. In a case of carrying out this opto-chemical treatment by the body cavity probe of FIG. 14, the injection of the tumor selectivity of the injected agent can be improved by carrying out the injection while monitoring the MR images obtained by this body cavity probe.

It is also to be noted that the imaging parameters of the MRI can be affected by the factors such as the temperature that can be changed by the treatment. Consequently, the timing for the MR image taking by this body cavity probe should be sufficiently separated from the timing for the treatment by this body cavity probe in order to remove the possible influence of the treatment from the obtained MR image, so that the accurate determination of treatment position or accurate judgement of treatment effect can be made on a basis of the MR image.

On the other hand, for the purpose of monitoring the treatment effect, the real time property is a crucial requirement, so that the high speed or ultra high speed imaging pulse sequence should be employed for this purpose, even though the S/N ratio must be sacrificed to some extent in such an imaging pulse sequence.

Now, these conflicting requirements of the high S/N ratio and the real time property can be resolved at least in some cases such as a case of treating the prostrate which is distributed around the body cavity. Namely, the treatment and the imaging can be carried out simultaneously in parallel, at sufficiently separated treatment region and imaging region sequentially, so as to improve the efficiency of the overall operation and realizing the satisfactory real time property without sacrificing the S/N ratio. In particular, in this case, the imaging time can be shortened by limiting the imaging regions to be sufficiently small, so that the high precision imaging can be achieved by the normal speed imaging pulse sequence such as that for the usual spin echo imaging.

Figure 15:
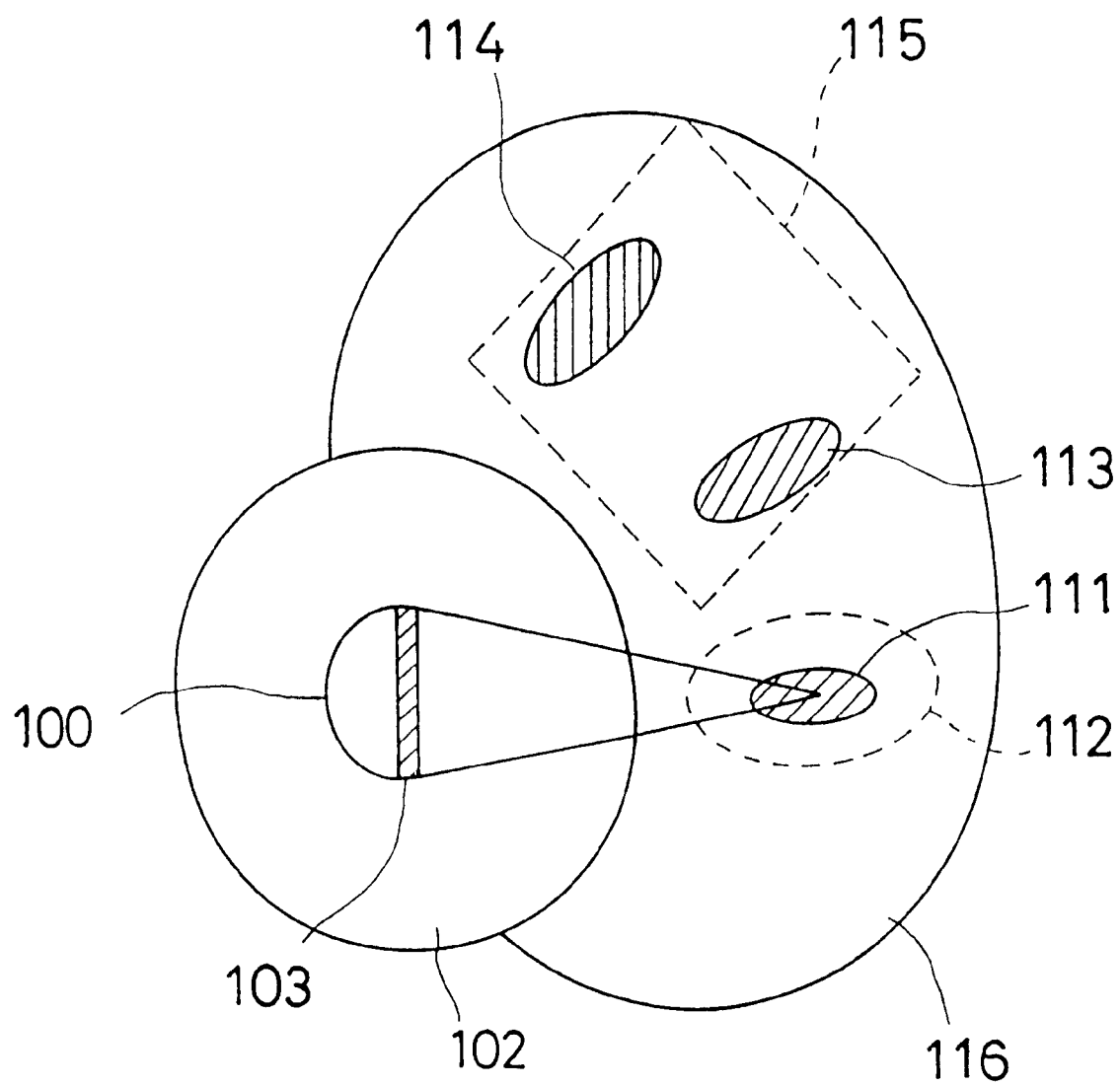
FIG. 15 is a diagrammatic illustration showing a possible operation procedure for the body cavity probe in the third embodiment of the present invention.

For example, when the treatment target portion 116 which is distributed as shown in FIG. 15 is going to be treated by the body cavity probe of FIG. 11, the ultrasonic waves can be irradiated onto one treatment target portion 111 within an area 112, while at the same time the MR image can be taken from an area 115 sufficiently separated from the area 102 to be free of the influence of the ultrasonic wave irradiation, for the purpose of judging the treatment effect on a previously treated treatment target portion 113 or determining the treatment position for a next treatment target portion 114 within this area 115, for example.

In this example of FIG. 15, the body cavity probe of FIG. 11 is used as the MR image can be taken uniformly in the circumferential direction in this body cavity probe. However, the body cavity probe equipped with a surface coil such as that shown in FIG. 9 which has the sensitivity only in one direction may also be adapted to the above procedure by enlarging the imaging region to be sufficiently larger than the region influenced by the treatment. In such a case, the selective excitation method can be employed in the MRI to realize the high resolution in a limited imaging region.

As described, according to this third embodiment, it becomes possible to obtain the MR images of the treatment target portion at a high resolution all the times, so that the initial positioning, the treatment effect confirmation, and the treatment monitoring can be realized in real time by using these MR images.

Figure 16:
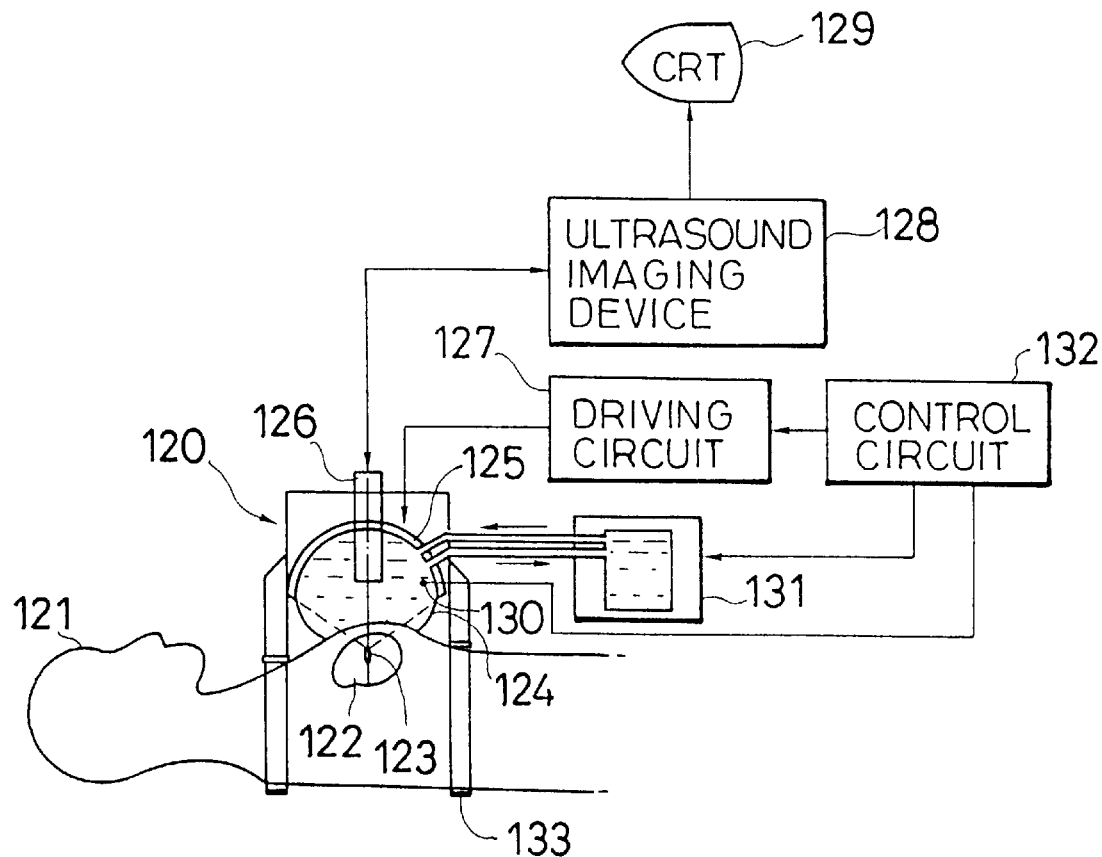
FIG. 16 is a partially cross sectional block diagram of a fourth embodiment of an ultrasonic wave medical treatment apparatus according to the present invention.

Referring now to FIG. 16, the fourth embodiment of the ultrasonic wave medical treatment apparatus according to the present invention will be described in detail. This fourth embodiment concerns with the modified configuration of the ultrasonic wave applicator in the ultrasonic wave medical treatment apparatus.

In this fourth embodiment, the ultrasonic wave applicator 120 comprises an ultrasonic transducer 125 formed by at least one piezoelectric elements for generating the ultrasonic waves, which is coupled with a patient 121 through a water bag 124 containing the coupling fluid. Here, the ultrasonic transducer 125 is driven by a driving circuit 127 to generate the ultrasonic waves focused on a focal point 123 located within a treatment target portion 122 of the patient 121.

The treatment is monitored by an ultrasound imaging device 128 which obtains a tomographic image on a plane containing the focal point 123 of the ultrasonic transducer 125 from the reflected ultrasound signals detected by an ultrasonic probe 126 mounted at a center of the ultrasonic transducer 125 and displays the obtained ultrasound tomographic image on a CRT 129.

The coupling fluid contained in the water bag 124 is cooled by being circulated by the a cooling device 131 according to the temperature of the coupling fluid within the water bag 124 measured by a temperature sensor 130, in order to prevent the potentially dangerous heat generation due to the ultrasonic wave irradiation at the ultrasonic transducer 125 and the body surface that can cause the burning of the body surface.

A control circuit 132 controls the driving circuit 127 and the cooling device 131 to control the irradiation of the ultrasonic waves, the change of the ultrasonic wave intensity, the setting of the cooling temperature, etc.

In this fourth embodiment, the ultrasonic wave applicator 120 is fixedly supported with respect to the patient's body by means of an applicator fixing belts 133 for binding the ultrasonic wave applicator 120 and the patient 121 together, so as to prevent the displacement of the focal point 123 of the ultrasonic transducer 125 in the ultrasonic wave applicator 120 which has been positioned with respect to the treatment target portion 122 within the patient's body due to the body movement or the respiration by the patient 121.

Figure 17:
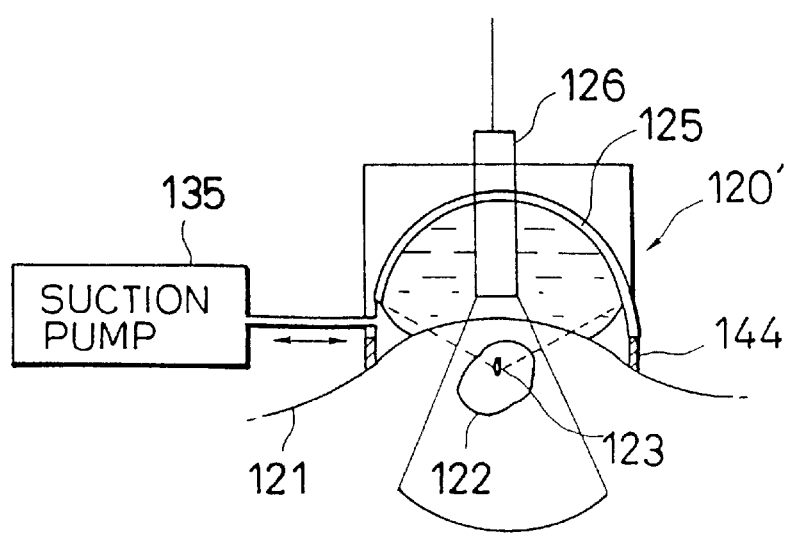
FIG. 17 is a cross sectional view of an alternative configuration for the ultrasonic wave applicator that can be used in the apparatus of FIG. 16.

Alternatively, instead of this ultrasonic wave applicator 120 using the applicator fixing belts 133, the ultrasonic wave applicator 120' may be formed as shown in FIG. 17 which is equipped with a rubber ring 144 at the edge of the ultrasonic wave applicator 120' for sucking onto the body surface, and a suction pump 135 for vacuuming the air from a space between the ultrasonic wave applicator 120' and the body surface enclosed by the rubber ring 144 after the rubber ring 144 is attached onto the body surface such that the ultrasonic wave applicator 120' can be fixedly supported with respect to the patient 121.

Figure 18:
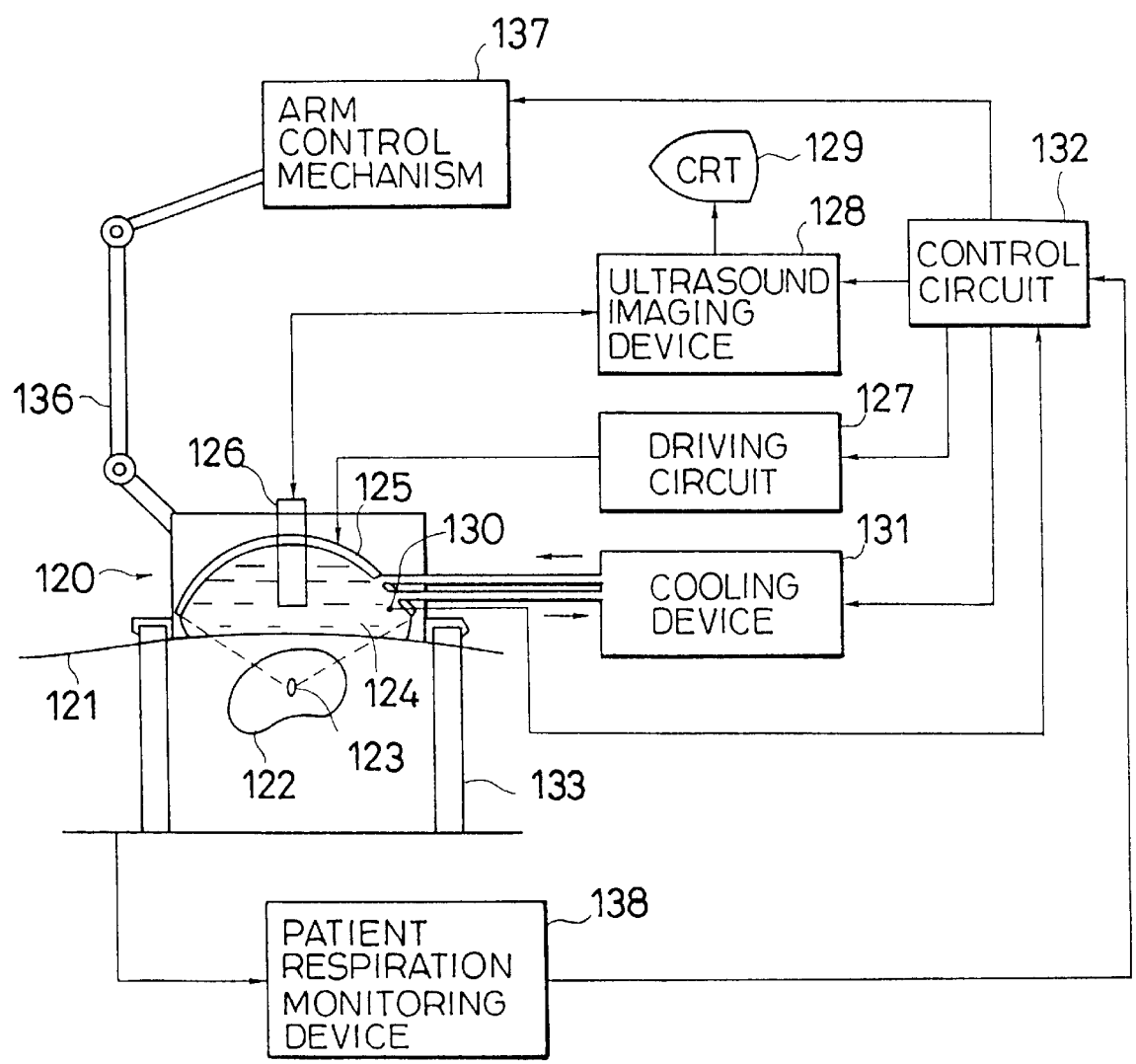
FIG. 18 is a partially cross sectional block diagram of one modified configuration for the apparatus of FIG. 16.

Also, in a case the weight of the ultrasonic wave applicator 120 is too heavy for the patient 121 to endure, the ultrasonic wave applicator 120 may be supported by a support arm 136 controlled by an arm control mechanism 137 as shown in FIG. 18.

In addition, by monitoring the respiration of the patient 121 by means of a patient respiration monitoring device 138, the arm control mechanism 137 can be controlled by the controller 132 such that the supporting arm 136 can set the ultrasonic wave applicator 120 in a motion which closely follows the patient's body movement due to the respiration, so as to prevent the displacement of the focal point 123 from the treatment target portion 122 as much as possible.

Figure 19:
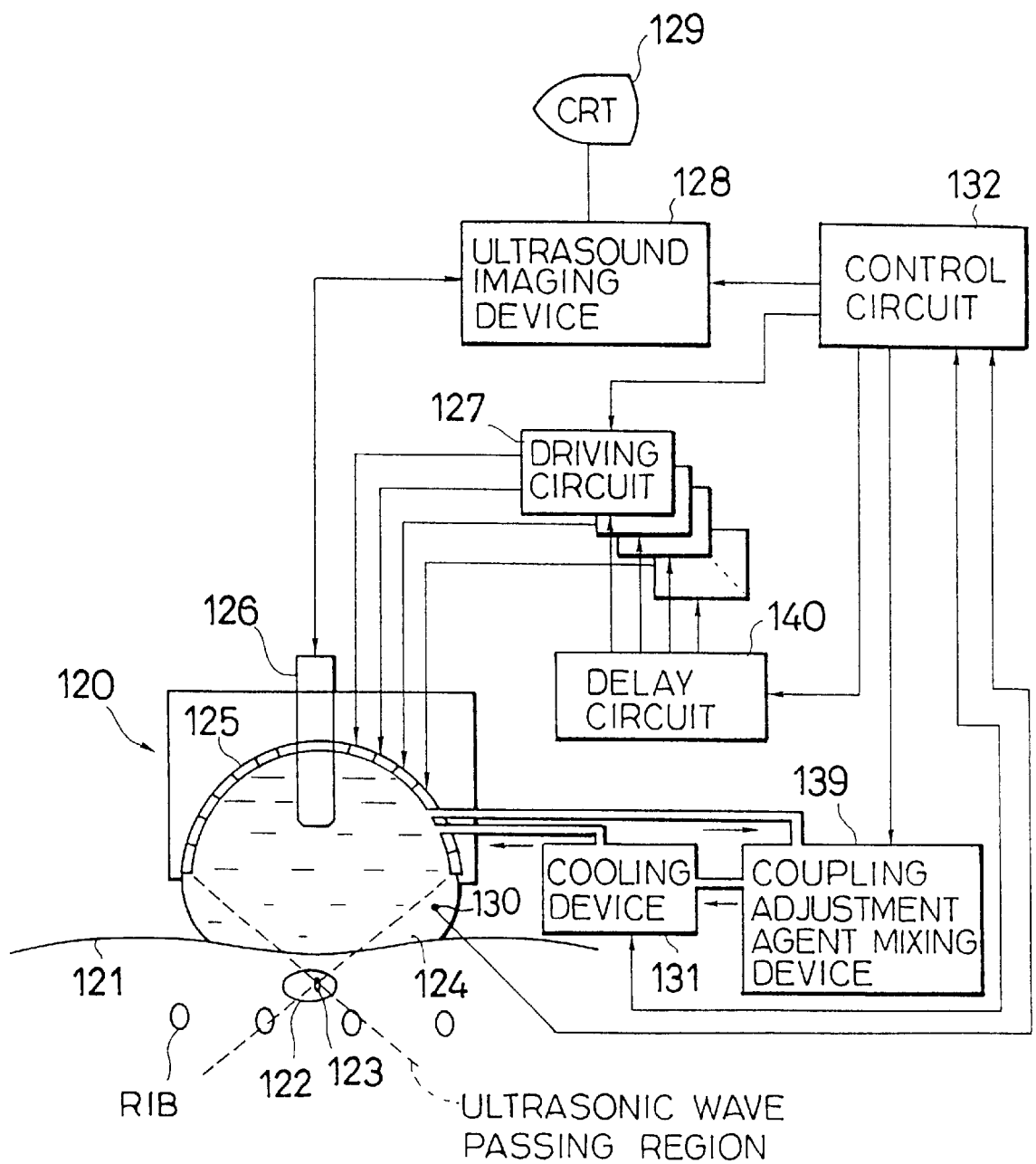
FIG. 19 is a partially cross sectional block diagram of another modified configuration for the apparatus of FIG. 16.

It is also possible to modify the configuration of FIG. 16 as shown in FIG. 19, in which a coupling adjustment agent mixing device 139 is provided in conjunction with the cooling device 131 so as to change the mixing rate of the water and the coupling adjustment agent in the coupling fluid.

Namely, in the treatment of the superficial tumors such as that of the breast cancer and the skin cancer, there is a need to lower the energy density of the ultrasonic waves within the ultrasonic wave passing region except for the focal point by widening the focusing angle of the ultrasonic waves in order to suppress the adverse side effect due to the heat generation at the body surface and the ribs located behind the focal point. In addition, it is expected that there is also a need to lower the temperature within the water bag 124 in order to cool the body surface further. However, when the temperature of the coupling fluid is lowered while the usually used water is employed as the coupling fluid, there arises a sonic speed difference between the water and the living tissues such that the ultrasonic waves are deflected at the boundary between them and the focus point of the ultrasonic waves is de-focused from an intended focal point position.

In order to cope with this problem, the coupling adjustment agent mixing device 139 changes the mixing rate of the water and the coupling adjustment agent in a form of a sonic speed adjustment agent such as the propanol according to the temperature of the coupling fluid within the water bag 124 so as to compensate the sonic speed difference between the coupling fluid and the living tissues and suppress the deflection of the ultrasonic waves.

In this case, the control circuit 132 has a table of data for the sonic speeds corresponding to various mixing rates of the sonic speed adjustment agent and the water at various temperatures, so that the control circuit 132 can determine the appropriate mixing rate according to this table of data, the temperature of the coupling fluid within the water bag 124, and the sonic speed in the living tissues, and controls the coupling adjustment agent mixing device 139 to realize the determined mixing rate such that the sonic speed in the coupling fluid becomes equal to that in the living tissues. Here, the sonic speed in the living tissues may be fixed to an approximate value of 1570 m/s for simplicity.

It is also possible to measure the actual sonic speeds in the coupling fluid and the living tissues as follows.

Figure 20A:
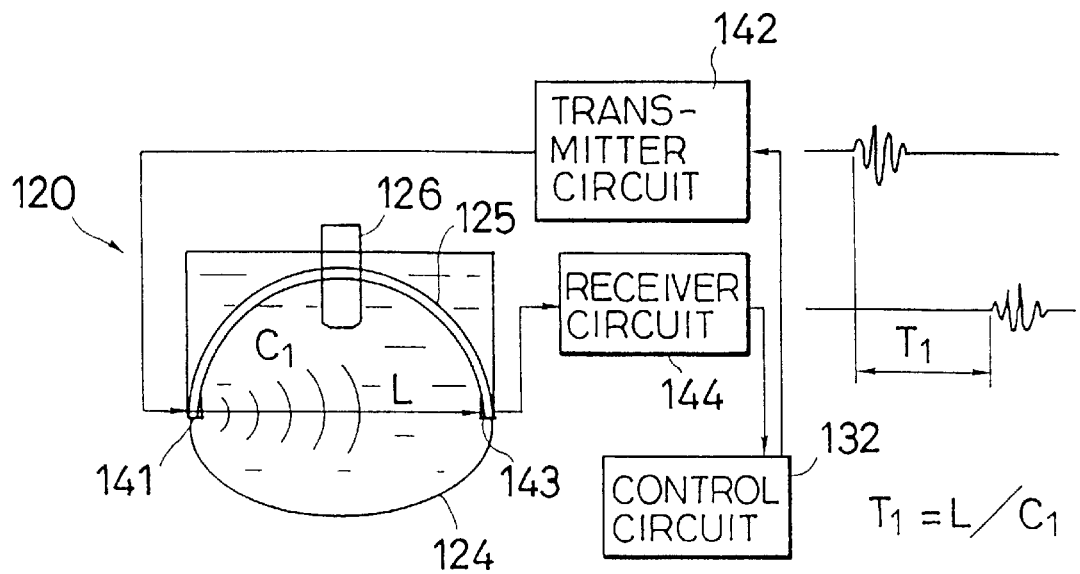
FIGS. 20A, 20B, and 20C are illustrations showing one scheme for measuring sonic speeds in the apparatus of FIG. 19.

Namely, the configuration of FIG. 19 can be modified as shown in FIG. 20A to incorporate a transmitting transducer 141 and a receiving transducer 143 on opposite sides at the edge of the ultrasonic transducer 125, which are connected with a transmitter circuit 142 and a receiver circuit 144, respectively, controlled by the control circuit 132.

In this configuration of FIG. 20A, the sonic speed in the coupling fluid is measured in a state in which the ultrasonic wave applicator 120 is not in contact with the body surface as follows. First, the control circuit 132 controls the transmitter circuit 142 to drive the transmitting transducer 141 to emit the ultrasonic wave which is subsequently propagated through the coupling fluid. Then, when the receiving transducer 143 receives the propagated ultrasonic wave, the receiver circuit 144 notifies this to the control circuit 132, such that the control circuit 132 calculates the propagation time T1 between the emission of the ultrasonic wave at the transmitting transducer 141 and the reception of the ultrasonic wave at the receiving transducer 143. Then, the control circuit 132 calculates the sonic speed C1 in the coupling fluid as a distance L between the transmitting transducer 141 and the receiving transducer 143 divided by the measured propagation time t1, i.e. C1=L/T1.

Figure 20B:
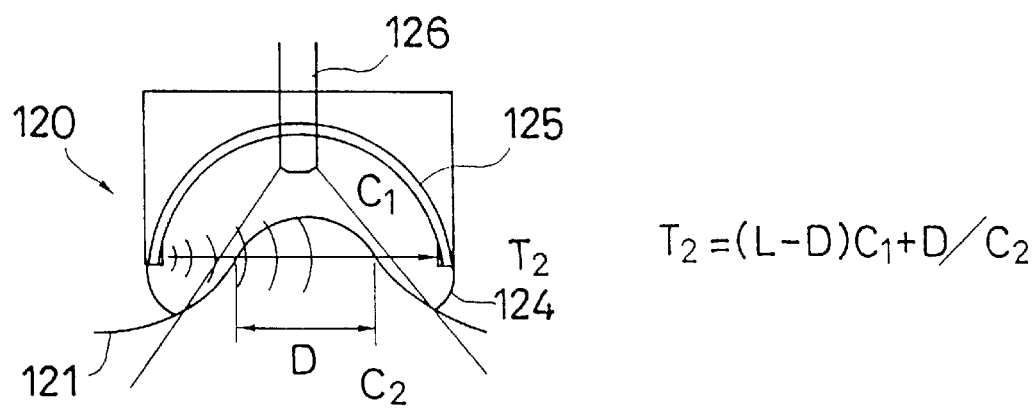
Figure 20C:
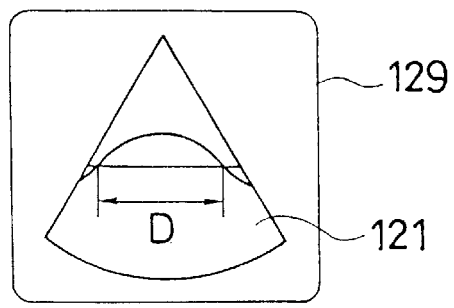

Next, the sonic speed in the living tissues is measured in a state in which the ultrasonic wave applicator 120 is in contact with the body surface by measuring the propagation time T2 similarly as shown in FIG. 20B, and calculating the sonic speed C2 in the living tissues according to:

$$T2=(L-D)C1+D/C2$$

where D is a length of the living tissues through which the ultrasonic wave propagated between the transmitting transducer 141 and the receiving transducer 143, which can be determined from the ultrasound image obtained by using the ultrasonic probe 126 and displayed on the CRT 129 as indicated in FIG. 20C.

Alternatively, it is also possible to measure the actual sonic speeds in the coupling fluid and the living tissues as follows.

Namely, the ultrasonic probe 126 which is made to be movably fixed by means of a pulse motor (not shown) is held to be vertical with respect to the body surface, and using an object within the patient's body such as a rib which has a large reflection echo as an ultrasonic marker 145, the ultrasonic wave applicator 120 or the ultrasonic probe 126 is moved such that the ultrasonic marker 145 is located on a central axis in the ultrasound image as shown in FIG. 21A, at which the ultrasonic image appears as shown in FIG. 21C. In this state (1), the propagation time t1 for the ultrasonic wave between the ultrasonic probe 126 and the body surface, the propagation time t2 for the ultrasonic wave between the ultrasonic probe 126 and the ultrasonic marker 145, and the height h between the ultrasonic probe 126 and the body surface are measured. Next, the ultrasonic wave applicator 120 or the ultrasonic probe 126 is inclined for an angle θ with respect to the body surface as in a state (2) shown in FIG. 21B, at which the ultrasound image appears as shown in FIG. 21D, and then moved in parallel to the body surface until the ultrasonic marker 145 comes on the central axis in the ultrasonic image as in a state (3) shown in FIG. 21B. at which the ultrasound image appears as shown in FIG. 21D. In these states (2) and (3), the length l indicated in FIG. 21B is measured. Then, the sonic speeds c1 and c2 in the coupling fluid and the living tissues are determined by solving the following four simultaneous equations from the measured values at the control circuit 132.

$$c1=2h/t1$$
$$d=c2((t1-t2)/2)$$
$$\sin \theta t/\sin \theta = c2/c1$$
$$\tan \theta t = l/d$$

where a depth d of the ultrasonic marker 145 and an angle θt are unknowns as indicated in FIG. 21B.

In this fourth embodiment, it is also possible to use the coupling adjustment agent other than the sonic speed adjustment agent such as a glycerol which functions as an acoustic impedance adjustment agent for adjusting the acoustic impedance of the coupling fluid to suppress the reflection of the ultrasonic waves at the body surface, rather than adjusting the sonic speed in the coupling fluid. In such a case, the deflection of the ultrasonic waves at the body surface due to the sonic speed difference can be compensated by using the ultrasonic transducer 125 of a phased array type and changing the driving phases of the driving circuit 127 for the piezoelectric elements of the ultrasonic transducer 125 by a delay circuit 140 shown in FIG. 19 to adjust the position of the focal point 123 such that the de-focusing due to the deflection can be compensated.

It is also to be noted that the propanol and the glycerol mentioned above may be replaced by any other known fluid materials having the similar functions as these such as other alcoholic acids in this fourth embodiment.

As described, according to this fourth embodiment, it becomes possible to maintain the relative position of the ultrasonic wave applicator with respect to the treatment target portion, and to secure the proper coupling of the ultrasonic waves from the ultrasonic wave applicator to the patient such that the accurate treatment of the patient can be realized.

Referring now to FIG. 22, the fifth embodiment of the ultrasonic wave medical treatment apparatus according to the present invention will be described in detail. This fourth embodiment concerns with the modified configuration of the ultrasonic wave applicator in the ultrasonic wave medical treatment apparatus.

In this fifth embodiment, the ultrasonic wave applicator 150 comprises an ultrasonic transducer 155 formed by at least one piezoelectric elements for generating the ultrasonic waves, which is coupled with a patient 151 through a water bag 154 containing the coupling fluid, and supported by an arm control mechanism 166. Here, the ultrasonic transducer 155 is driven by a driving signal generated by a signal generator 159 and transmitted via an amplifier 158, an impedance matching circuit 157, and a wattmeter 156, to generate the ultrasonic waves focused on a focal point 153 located within a treatment target portion 152 of the patient 151.

The treatment is monitored by an ultrasound imaging device 161 which obtains a tomographic image on a plane containing the focal point 153 of the ultrasonic transducer 155 from the reflected ultrasound signals detected by an ultrasonic probe 160 mounted on the ultrasonic wave applicator 150 and displays the obtained ultrasound tomographic image on a CRT 162.

The coupling fluid contained in the water bag 154 is cooled by being circulated by the a cooling device 164 in order to prevent the potentially dangerous heat generation due to the ultrasonic wave irradiation at the ultrasonic transducer 155 and the body surface that can cause the burning of the body surface.

A control circuit 163 is equipped with a console 165 and controls the ultrasonic imaging device 161 and the arm control mechanism 166, as well as the signal generator 159, and the cooling device 164 to control the irradiation of the ultrasonic waves, the change of the ultrasonic wave intensity, the driving frequency of the ultrasonic transducer 155, the setting of the cooling temperature, etc.

Figure 23A:
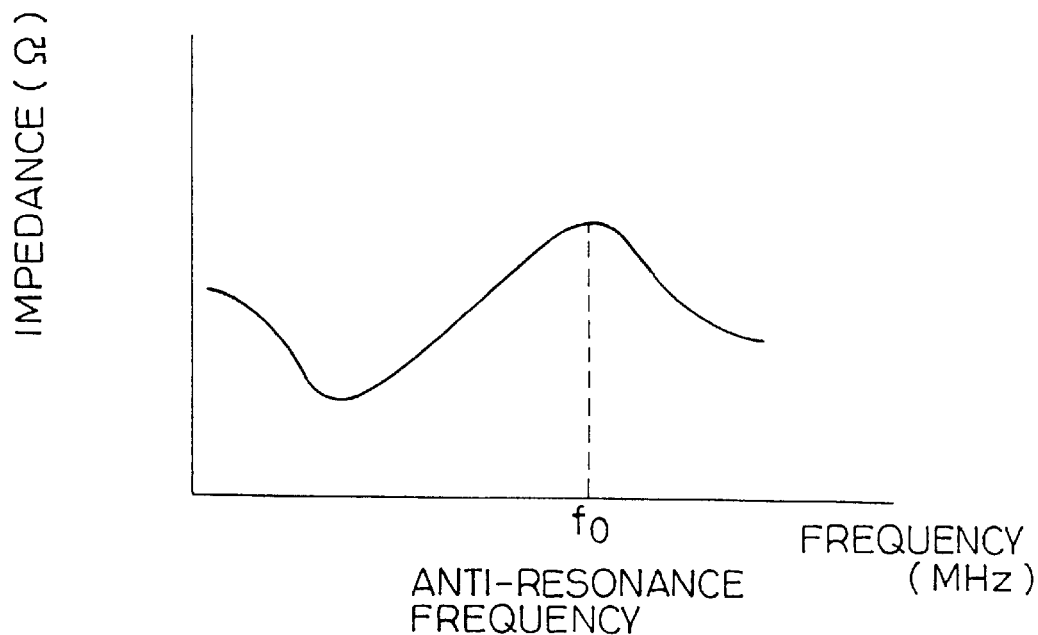
FIGS. 23A and 23B are graphs showing impedance and reflected electric power characteristics as a function of frequency, respectively, in the apparatus of FIG. 22.
Figure 23B:
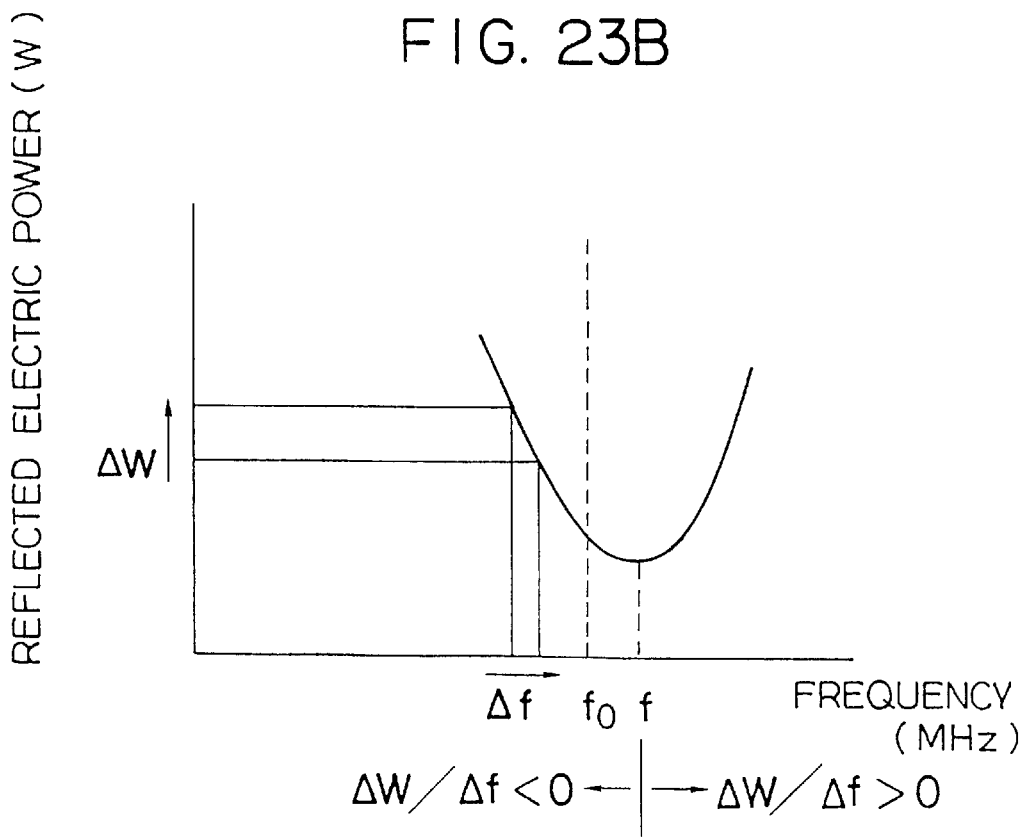

Now, in general, the piezoelectric elements of the ultrasonic transducer 155 has a fixed mechanical resonance frequency determined by their thickness, and this mechanical resonance frequency coincides with an anti-resonance frequency in the electric impedance characteristic of these piezoelectric elements, as indicated in FIGS. 23A and 23B. In theory, the electrically most efficient manner of using these piezoelectric elements will be to carry out a tuning at this frequency to make the impedance matching with the output impedance of the amplifier 158 at the impedance matching circuit 157.

However, in practice, there arises a phenomenon in which the impedance matching point is gradually deviated as the electric and mechanical resonance characteristic of the piezoelectric elements changes due to the heat generation of the piezoelectric elements themselves or the heat generation of the matching elements such as inductance L and a capacitance C at a time of high power input.

In order to suppress this phenomenon, the control circuit 163 controls the driving frequency of the signal generator 159 by monitoring the passing electric powers in the normal and reverse directions at the wattmeter 156 such that the reflected electric power from the piezoelectric elements becomes minimum. Here, the acoustic output cannot be obtained when the driving frequency of the piezoelectric elements largely deviates from the mechanical resonance frequency of the piezoelectric elements, so that the driving frequency is made to be variable within a range of ±15% of the mechanical resonance frequency.

The driving frequency can be determined by obtaining the change $\Delta W$ of the reflected electric power in response to the change of the driving frequency from the current driving frequency by $\Delta f$, and controlling the driving frequency in a direction to make $\Delta W/\Delta f$ minimum as indicated in FIG. 23B. At this point, the impedance for the output terminal of the amplifier 158 changes as the driving frequency changes, so that the electric power inputted into the piezoelectric elements also changes, and therefore the control circuit 163 also controls the driving voltage of the signal generator 159 such that the input energy at the focal point 153 of the ultrasonic waves per unit time becomes constant.

It is to be noted here that, instead of controlling the driving voltage of the signal generator 159 to make the input energy at the focal point 153 per unit time to be constant as described above, it is also possible to control the driving voltage of the signal generator 159 to make the peak intensity at the focal point 153 to be constant.

In addition, it is known that the heat generation at the focal point 153 is proportional to the cube of the frequency because of the frequency dependence of the focusing effect and the attenuation rate of the ultrasonic waves, so that in view of this fact, the theoretical value for the heat generation at the focal point 153 can be calculated from the frequency, the input power, and the electro-mechanical conversion efficiency, and the driving voltage of the signal generator 159 can be controlled to make this calculated heat generation at the focal point 153 to be constant instead.

Figure 24:
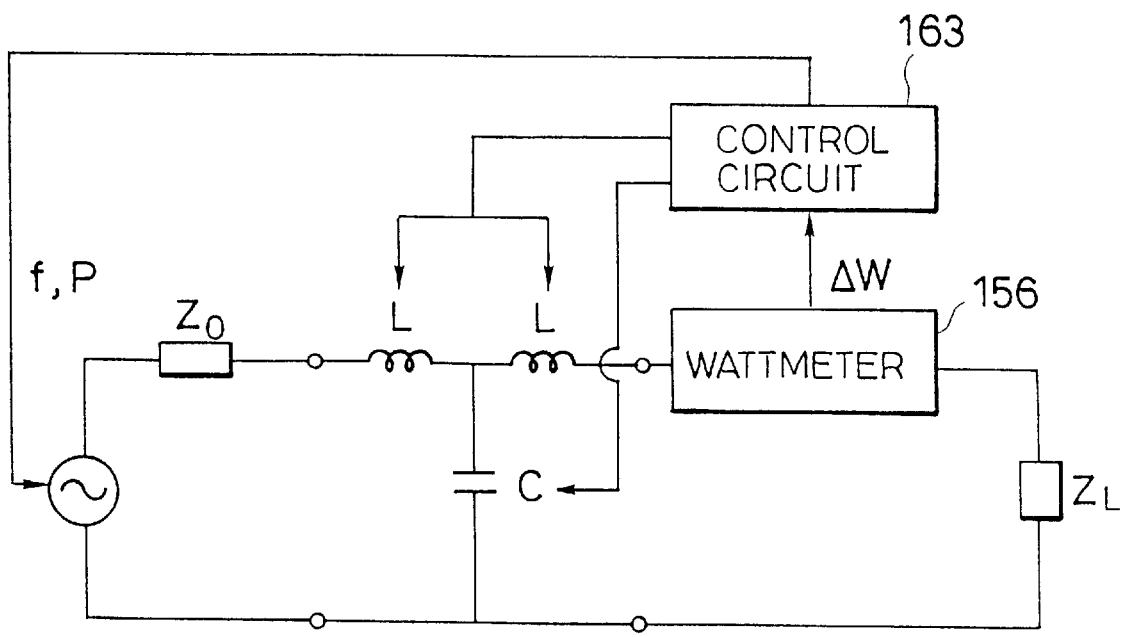
FIG. 24 is an equivalent circuit diagram for an alternative configuration of an impedance matching circuit in the apparatus of FIG. 22.

It is also to be noted that, instead of correcting the impedance matching by changing the driving frequency on the driving side as described above, the inductance L and the capacitance C of the impedance matching circuit 157 can be made to be variable, and the control circuit 163 can control the impedance in a state of maintaining the following relationship:

$$\omega^2 LC = 1$$

where $\omega = 2\pi f$ and f is the driving frequency, to make the reflected electric power becomes minimum, by means of a circuit configuration as indicated by an equivalent circuit diagram shown in FIG. 24.

As a variation of this fifth embodiment, the control circuit 163 can also control the driving frequency of the signal generator 159, either step-wise or continuously, while the ultrasonic waves are irradiated from the ultrasoic wave applicator 150 onto the treatment target portion 153, in order to suppress the cavitations generated at a time of a high power input.

Namely, by controlling the driving frequency in this manner, even when the cavitation in size dependent on the driving frequency is generated at the focal point region, it will disappear as the driving frequency is changed. Of course, the new cavitation in size dependent on the changed driving frequency is going to be newly generated instead, but the generation and the growing of the new cavitation takes a considerable time so that the generation of the cavitation becomes much harder compared with a case of using a fixed driving frequency.

As a consequence, it becomes possible to prevent the occurrence of the undesirable situations such as the insufficient treatment resulting from the failure of the ultrasonic waves to reach to the intended treatment target portion, or the larger than expected heat generation in front of the intended focal point due to the scattering of the ultrasonic waves by the cavitations generated in front of the intended focal point, and therefore it becomes possible to make more accurate and safe treatment.

As described, according to this fifth embodiment, it becomes possible to realize the impedance matching by simply adjusting the driving frequency for the ultrasonic transducer, and to suppress the generation of the cavitations by actively changing the driving frequency constantly, such that the effective, efficient, and safe treatment of the patient can be realized.

It is to be noted here that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. An ultrasonic wave medical treatment apparatus, comprising:

an MRI device for taking MR images of a patient, including a surface coil for receiving MR signals in taking the MR images; and an ultrasonic wave treatment device for treating a treatment target, portion within the patient by irradiating ultrasonic waves thereon in accordance with the MR images taken by the MRI device, including an ultrasonic wave generator for generating ultrasonic waves focused onto the treatment target portion, wherein the surface coil of the MRI device is provided on the ultrasonic wave generator.

2. The apparatus of claim 1, wherein the ultrasonic wave generator is in a form of an ultrasonic wave applicator for generating the ultrasonic waves focused onto the treatment target portion having an ultrasonic transducer for generating the ultrasonic waves and a water bag for containing a coupling fluid for leading the ultrasonic waves generated by the ultrasonic transducer to a body surface of the patient by making a contact with the body surface, and the surface coil of the MRI device is attached on a surface film of the water bag.

3. The apparatus of claim 2, wherein the ultrasonic transducer has electrodes with a plurality of slits formed thereon.

4. The apparatus of claim 1, wherein the ultrasonic wave generator is in a form of an ultrasonic wave applicator for generating the ultrasonic waves focused onto the treatment target portion having spike shaped pointers for pointing a focal point of the ultrasonic waves.

5. The apparatus of claim 4, wherein the MRI device is configured to take MR images with the ultrasonic wave applicator attached to the patient so as to obtain MR images in which images of the spike shaped pointers indicate a position of the focal point of the ultrasonic waves.

6. The apparatus of claim 1, wherein the ultrasonic wave generator is in a form of a body cavity probe to be inserted into a body cavity of the patient near the treatment target portion having an ultrasonic transducer for generating the ultrasonic waves focused onto the treatment target portion, and the surface coil of the MRI device is provided on the body cavity probe.

7. The apparatus of claim 6, wherein the MRI device is configured to operate the surface coil as an RF coil for transmitting RF pulses.

8. The apparatus of claim 6, wherein the body cavity probe has a balloon for fixing a position of the body cavity probe within the body cavity by being expanded to press against the body cavity, and the surface coil is attached on the balloon.

9. The apparatus of claim 8, wherein the balloon contains an inner balloon and an outer balloon and the surface coil is attached on the inner balloon.

10. The apparatus of claim 9, wherein the inner balloon is freely rotatable and translatable within the outer balloon.

11. The apparatus of claim 6, wherein the surface coil is in a form of a solenoid coil.

12. The apparatus of claim 11, wherein the ultrasonic transducer is freely rotatable and translatable with respect to the surface coil.

13. The apparatus of claim 6, wherein the body cavity probe has a balloon for fixing a position of the body cavity probe within the body cavity by being expanded to press against the body cavity, and the ultrasonic transducer and the surface coil are provided on one side of the body cavity probe while the balloon is provided on another side opposite to said one side of the body cavity probe.

14. The apparatus of claim 6, wherein the ultrasonic transducer and the surface coil are provided coaxially in the body cavity probe.

15. The apparatus of claim 6, wherein while the ultrasonic transducer generates the ultrasonic waves focused onto one part of the treatment target portion, the MRI device takes the MR images of another part of the treatment target portion separated from said one part simultaneously.

* * * * *